United States Patent
Bryans et al.

(10) Patent No.: US 6,689,906 B1
(45) Date of Patent: Feb. 10, 2004

(54) BICYCLIC AMINO ACIDS AS PHARMACEUTICAL AGENTS

(75) Inventors: Justin Stephen Bryans, Balsham (GB); David Clive Blakemore, Cambridge (GB); Simon Andrew Osborne, Suffolk (GB); Jean-Marie Receveur, Montpellier (FR)

(73) Assignee: Warner-Lambert Company, Morris Plains, NJ (US)

( * ) Notice: Subject to any disclaimer, the term of this patent is extended or adjusted under 35 U.S.C. 154(b) by 69 days.

(21) Appl. No.: 10/130,023

(22) PCT Filed: Oct. 17, 2000

(86) PCT No.: PCT/US00/28687
§ 371 (c)(1),
(2), (4) Date: Apr. 19, 2002

(87) PCT Pub. No.: WO01/28978
PCT Pub. Date: Apr. 26, 2001

Related U.S. Application Data

(60) Provisional application No. 60/160,725, filed on Oct. 20, 1999.

(51) Int. Cl.$^7$ ............................................. C07C 61/06
(52) U.S. Cl. .................... 562/503; 514/530; 514/572; 514/573
(58) Field of Search ..................... 562/503; 514/572, 514/573, 530

(56) References Cited

FOREIGN PATENT DOCUMENTS

| | | |
|---|---|---|
| FR | 2052979 | 6/1970 |
| FR | 2294697 A | 12/1975 |
| WO | 9921824 | 5/1999 |

*Primary Examiner*—Paul J. Killos
(74) *Attorney, Agent, or Firm*—David R. Kurlandsky; Charles W. Ashbrook

(57) ABSTRACT

The invention is a novel series of cyclic amino acids which are useful in the treatment of epilepsy, faintness attacks, neurodegenerative disorders, depression, anxiety, panic, pain, neuropathological disorders, gastrointestinal disorders such as irritable bowel syndrome (IBS), and inflammation, especially arthritis. A pharmaceutical composition containing a compound of the invention as well as methods of preparing the compounds and novel intermediates useful in the preparation of the final compounds are included.

16 Claims, No Drawings

BICYCLIC AMINO ACIDS AS PHARMACEUTICAL AGENTS

CROSS-REFERENCE TO RELATED APPLICATIONS

This application is a 371 application of PCT/US00/28687 filed Oct. 17, 2000, which claims the benefit of priority to United States provisional application Serial No. 60/160,725 filed Oct. 20, 1999.

BACKGROUND OF THE INVENTION

Compounds of formula

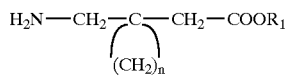

wherein $R_1$ is hydrogen or a lower alkyl radical and n is 4, 5, or 6 are known in U.S. Pat. No. 4,024,175 and its divisional U.S. Pat. No. 4,087,544. The uses disclosed are: protective effect against cramp induced by thiosemicarbazide; protective action against cardiazole cramp; the cerebral diseases, epilepsy, faintness attacks, hypokinesia, and cranial traumas; and improvement in cerebral functions. The compounds are useful in geriatric patients. The patents are hereby incorporated by reference.

SUMMARY OF THE INVENTION

The instant invention is a series of novel bicyclic amino acids, their pharmaceutically acceptable salts, and the prodrugs of the amino acids.

The compounds are those of formula:

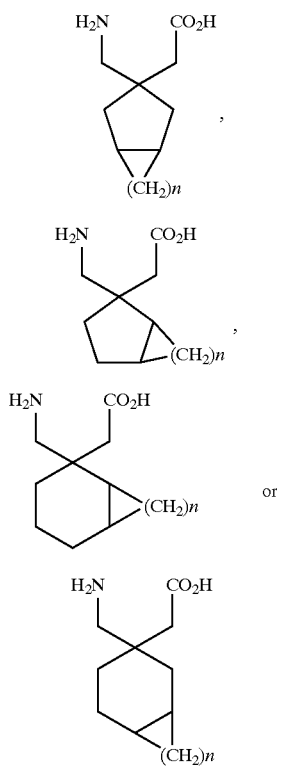

wherein n is an integer of from 1 to 4, where there are stereocenters, each center may be independently R or S.

Preferred compounds of the invention are those of Formulae I–IV above wherein n is an integer of from 2 to 4. Other preferred compounds are those of Formula I above. Especially preferred compounds are:

(1α,6α,8β)(2-Aminomethyl-octahydro-inden-2-yl)-acetic acid;

(2-Aminomethyl-octahydro-inden-2-yl)-acetic acid;

(2-Aminomethyl-octahydro-pentalen-2-yl)-acetic acid;

(2-Aminomethyl-octahydro-pentalen-2-yl)-acetic acid;

(3-Aminomethyl-bicyclo[3.2.0]hept-3-yl)-acetic acid;

(3-Aminomethyl-bicyclo[3.2.0]hept-3-yl)-acetic acid; and (2-Aminomethyl-octahydro-inden-2-yl)-acetic acid.

Other preferred compounds are those selected from (1α,5β)(3-Aminomethyl-bicyclo[3.1.0]hex-3-yl)-acetic acid, (1α,5β)(3-Aminomethyl-bicyclo[3.2.0]hept-3-yl)-acetic acid, (1α,5β)(2-Aminomethyl-octahydro-pentalen-2-yl)-acetic acid, (1α,6β)(2-Aminomethyl-octahydro-inden-2-yl)-acetic acid, (1α,7β)(2-Aminomethyl-decahydro-azulen-2-yl)-acetic acid, (1α,5β)(3-Aminomethyl-bicyclo[3.1.0]hex-3-yl)-acetic acid, (1α,5β)(3-Aminomethyl-bicyclo[3.2.0]hept-3-yl)-acetic acid, (1α,5β)(2-Aminomethyl-octahydro-pentalen-2-yl)-acetic acid, (1α,6β)(2-Aminomethyl-octahydro-inden-2-yl)-acetic acid, (1α,7β)(2-Aminomethyl-decahydro-azulen-2-yl)-acetic acid, (1α,3α,5α)(3-Aminomethyl-bicyclo[3.1.0]hex-3-yl)-acetic acid, (1α,3α,5α)(3-Aminomethyl-bicyclo[3.2.0]hept-3-yl)-acetic acid, (1α,3α,5α)(2-Aminomethyl-octahydro-pentalen-2-yl)-acetic acid, (1α,6α,8α)(2-Aminomethyl-octahydro-inden-2-yl)-acetic acid, (1α,7α,9α)(2-Aminomethyl-decahydro-azulen-2-yl)-acetic acid, (1α,3β,5α)(3-Aminomethyl-bicyclo[3.1.0]hex-3-yl)-acetic acid, (1α,3β,5α)(3-Aminomethyl-bicyclo[3.2.0]hept-3-yl)-acetic acid, (1α,3β,5α)(2-Aminomethyl-octahydro-pentalen-2-yl)-acetic acid, (1α,6α,8β)(2-Aminomethyl-octahydro-inden-2-yl)-acetic acid, (1α,7α,9β)(2-Aminomethyl-decahydro-azulen-2-yl)-acetic acid, ((1R,3R,6R)-3-Aminomethyl-bicyclo[4.1.0]hept-3-yl)-acetic acid, ((1R,3S,6R)-3-Aminomethyl-bicyclo[4.1.0]hept-3-yl)-acetic acid, ((1S,3S,6S)-3-Aminomethyl-bicyclo[4.1.0]hept-3-yl)-acetic acid, ((1S,3R,6S)-3-Aminomethyl-bicyclo[4.1.0]hept-3-yl)-acetic acid, ((1R,3R,6S)-3-Aminomethyl-bicyclo[4.2.0]oct-3-yl)-acetic acid,
((1R,3S,6S)-3-Aminomethyl-bicyclo[4.2.0]oct-3-yl)-acetic acid,
((1S,3S,6R)-3-Aminomethyl-bicyclo[4.2.0]oct-3-yl)-acetic acid,
((1S,3R,6R)-3-Aminomethyl-bicyclo[4.2.0]oct-3-yl)-acetic acid,
((3αR,5R,7αS)-5-Aminomethyl-octahydro-inden-5-yl)-acetic acid,
((3αR,5S,7αS)-5-Aminomethyl-octahydro-inden-5-yl)-acetic acid,
((3αS,5S,7αR)-5-Aminomethyl-octahydro-inden-5-yl)-acetic acid,
((3αS,5R,7αR)-5-Aminomethyl-octahydro-inden-5-yl)-acetic acid,
((2R,4αS,8αR)-2-Aminomethyl-decahydro-naphthalen-2-yl)-acetic acid,
((2S,4αS,8αR)-2-Aminomethyl-decahydro-naphthalen-2-yl)-acetic acid,
((2S,4αS,8αS)-2-Aminomethyl-decahydro-naphthalen-2-yl)-acetic acid,
((2R,4αR,8αS)-2-Aminomethyl-decahydro-naphthalen-2-yl)-acetic acid,
((2R,4αS,9αR)-2-Aminomethyl-decahydro-benzocyclohepten-2-yl)-acetic acid,
((2S,4αS,9αR)-2-Aminomethyl-decahydro-benzocyclohepten-2-yl)-acetic acid,
((2S,4αR,9αS)-2-Aminomethyl-decahydro-benzocyclohepten-2-yl)-acetic acid,
((2R,4αR,9αS)-2-Aminomethyl-decahydro-benzocyclohepten-2-yl)-acetic acid,
((1R,3R,6S)-3-Aminomethyl-bicyclo[4.1.0]hept-3-yl)-acetic acid,
((1R,3S,6S)-3-Aminomethyl-bicyclo[4.1.0]hept-3-yl)-acetic acid,
((1S,3S,6R)-3-Aminomethyl-bicyclo[4.1.0]hept-3-yl)-acetic acid,
((1S,3R,6R)-3-Aminomethyl-bicyclo[4.1.0]hept-3-yl)-acetic acid,
((1R,3R,6R)-3-Aminomethyl-bicyclo[4.2.0]oct-3-yl)-acetic acid,
((1R,3S,6R)-3-Aminomethyl-bicyclo[4.2.0]oct-3-yl)-acetic acid,
((1S,3S,6S)-3-Aminomethyl-bicyclo[4.2.0]oct-3-yl)-acetic acid,
((1S,3R,6S)-3-Aminomethyl-bicyclo[4.2.0]oct-3-yl)-acetic acid,
((3αR,5R,7αR)-5-Aminomethyl-octahydro-inden-5-yl)-acetic acid,
((3αR,5S,7αR)-5-Aminomethyl-octahydro-inden-5-yl)-acetic acid,
((3αS,5S,7αS)-5-Aminomethyl-octahydro-inden-5-yl)-acetic acid,
((3αS,5R,7αS)-5-Aminomethyl-octahydro-inden-5-yl)-acetic acid,
((2R,4αR,8αR)-2-Aminomethyl-decahydro-naphthalen-2-yl)-acetic acid,
((2S,4αS,8αR)-2-Aminomethyl-decahydro-naphthalen-2-yl)-acetic acid,
((2S,4αR,8αS)-2-Aminomethyl-decahydro-naphthalen-2-yl)-acetic acid,
((2R,4αS,8αS)-2-Aminomethyl-decahydro-naphthalen-2-yl)-acetic acid,
((2R,4αR,9αR)-2-Aminomethyl-decahydro-benzocyclohepten-2-yl)-acetic acid,
((2S,4αR,9αR)-2-Aminomethyl-decahydro-benzocyclohepten-2-yl)-acetic acid,
((2S,4αS,9αS)-2-Aminomethyl-decahydro-benzocyclohepten-2-yl)-acetic acid, and
((2R,4αS,9αS)-2-Aminomethyl-decahydro-benzocyclohepten-2-yl)-acetic acid.

The compounds of the invention are useful in treating a variety of disorders. The disorders include: epilepsy, faintness attacks, hypokinesia, cranial disorders, neurodegenerative disorders, depression, anxiety, panic, pain, neuropathological disorders, and sleep disorders.

Intermediates useful in the preparation of the final products are also included in the scope of the invention.

DETAILED DESCRIPTION

The compounds of the instant invention, their prodrugs, and their pharmaceutically acceptable salts are as defined above in Formulae I–IV.

Pharmaceutical compositions comprising a therapeutically effective amount of a compound of Formulas I–VII above are included in the instant invention.

Methods of using the compounds of the invention as agents for treating epilepsy, faintness attacks, hypokinesia, cranial disorders, neurodegenerative disorders, depression, anxiety, panic, pain, neuropathological disorders, sleep disorders, and premenstrual syndrome are part of the invention.

Since amino acids are amphoteric, pharmacologically compatible salts when R is hydrogen can be salts of appropriate inorganic or organic acids, for example, hydrochloric, sulphuric, phosphoric, acetic, oxalic, lactic, citric, malic, salicylic, malonic, maleic, succinic, and ascorbic. Starting from corresponding hydroxides or carbonates, salts with alkali metals or alkaline earth metals, for example, sodium, potassium, magnesium, or calcium are formed. Salts with quaternary ammonium ions can also be prepared with, for example, the tetramethyl-ammonium ion.

Prodrugs of compounds I–VIII are included in the scope of the instant invention. Aminoacyl-glycolic and -lactic esters are known as prodrugs of amino acids (Wermuth C. G., *Chemistry and Industry*, 1980:433–435). The carbonyl group of the amino acids can be esterified by known means. Prodrugs and soft drugs are known in the art (Palomino E., *Drugs of the Future*, 1990;15(4):361–368). The last two citations are hereby incorporated by reference.

The effectiveness of an orally administered drug is dependent upon the drug's efficient transport across the mucosal epithelium and its stability in entero-hepatic circulation. Drugs that are effective after parenteral administration but less effective orally, or whose plasma half-life is considered too short, may be chemically modified into a prodrug form.

A prodrug is a drug which has been chemically modified and may be biologically inactive at its site of action, but which may be degraded or modified by one or more enzymatic or other in vivo processes to the parent bioactive form.

This chemically modified drug, or prodrug, should have a different pharmacokinetic profile to the parent, enabling easier absorption across the mucosal epithelium, better salt formulation and/or solubility, improved systemic stability (for an increase in plasma half-life, for example). These chemical modifications may be 1) ester or amide derivatives which may be cleaved by, for example, esterases or lipases. For ester derivatives, the ester is derived from the carboxylic acid moiety of the drug molecule by known means. For amide derivatives, the amide may be derived from the carboxylic acid moiety or the amine moiety of the drug molecule by known means.

2) peptides which may be recognized by specific or nonspecific proteinases. A peptide may be coupled to the drug molecule via amide bond formation with the amine or carboxylic acid moiety of the drug molecule by known means.

3) derivatives that accumulate at a site of action through membrane selection of a prodrug form or modified prodrug form, 4) any combination of 1 to 3.

Current research in animal experiments has shown that the oral absorption of certain drugs may be increased by the preparation of "soft" quaternary salts. The quaternary salt is termed a "soft" quaternary salt since, unlike normal quaternary salts, e.g., $R-N^+(CH_3)_3$, it can release the active drug on hydrolysis.

"Soft" quaternary salts have useful physical properties compared with the basic drug or its salts. Water solubility may be increased compared with other salts, such as the hydrochloride, but more important there may be an increased absorption of the drug from the intestine. Increased absorption is probably due to the fact that the "soft" quaternary salt has surfactant properties and is capable of forming micelles and unionized ion pairs with bile acids, etc., which are able to penetrate the intestinal epithelium more effectively. The prodrug, after absorption, is rapidly hydrolyzed with release of the active parent drug.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention possess one or more chiral centers and each center may exist in the R(D) or S(L) configuration. The present invention includes all enantiomeric and epimeric forms as well as the appropriate mixtures thereof. For example, the compound of Example 2 is a mixture of all four possible stereoisomers. The compound of Example 6 is one of the isomers. The configuration of the cyclohexane ring carbon centers may be R or S in these compounds where a configuration can be defined.

The radioligand binding assay using [$^3$H]gabapentin and the $\alpha_2\delta$ subunit derived from porcine brain tissue was used (Gee N. S., Brown J. P., Dissanayake V. U. K., Offord J., Thurlow R., Woodruff G. N., "The Novel Anti-convulsant Drug, Gabapentin, Binds to the $\alpha_2\delta$ Subunit of a Calcium Channel," *J. Biol. Chem.*, 1996;271:5879–5776).

TABLE 1

| Compound | Structure | $\alpha_2\delta$ binding affinity ($\mu$M) |
| --- | --- | --- |
| ((1α,6α,8β)(2-Aminomethyl-octahydro-inden-2-yl)-acetic acid | 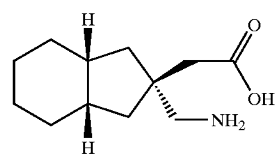 | >10 |
| (1α,6α,8α)(2-Aminomethyl-octahydro-inden-2-yl)-acetic acid | 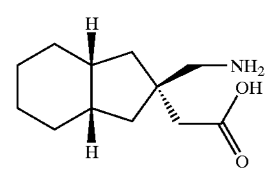 | 0.72 |
| (1α,3α,5α)(2-Aminomethyl-octahydro-pentalen-2-yl)-acetic acid | 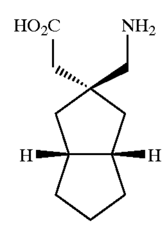 | 1.58 |
| (+/−)-(1α,5β)(2-Aminomethyl-octahydro-pentalen-2-yl)-acetic acid | 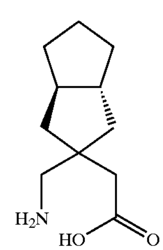 | >10 |

TABLE 1-continued

| Compound | Structure | α₂δ binding affinity (μM) |
|---|---|---|
| (1α,3α,5α)(3-Aminomethyl-bicyclo[3.2.0]hept-3-yl)-acetic acid | | 0.038 |
| (+/−)-(1α,5β)(3-Aminomethyl-bicyclo[3.2.0]hept-3-yl)-acetic acid | | 2.86 |
| (+/−)-(1α,6β)(2-Aminomethyl-octahydro-inden-2-yl)-acetic acid | | >10 |
| ((1α,3β,5α)(3-Aminomethyl-bicyclo[3.2.0]hept-3-yl)-acetic acid | | 0.332 |
| ((1α,3β,5α)(2-Aminomethyl-octahydro-pentalen-2-yl)-acetic acid | | |

Table 1 above shows the binding affinity of the compounds of the invention to the α₂δ subunit.

The compounds of the invention are compared to Neurontin®, a marketed drug effective in the treatment of such disorders as epilepsy. Neurontin® is 1-aminomethyl)-cyclohexaneacetic acid of structural formula

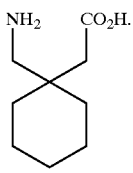

Gabapentin (Neurontin®) is about 0.10 to 0.12 μM in this assay. The compounds of the instant invention are expected, therefore, to exhibit pharmacologic properties comparable to gabapentin. For example, as agents for the treatment of convulsions, anxiety, and pain.

The present invention also relates to therapeutic use of the compounds of the mimetic as agents for neurodegenerative disorders.

Such neurodegenerative disorders are, for example, Alzheimer's disease, Huntington's disease, Parkinson's disease, and Amyotrophic Lateral Sclerosis.

The present invention also covers treating neurodegenerative disorders termed acute brain injury. These include but are not limited to: stroke, head trauma, and asphyxia Stroke refers to a cerebral vascular disease and may also be referred to as a cerebral vascular incident (CVA) and includes acute thromboembolic stroke. Stroke includes both focal and global ischemia Also, included are transient cerebral ischemic attacks and other cerebral vascular problems accompanied by cerebral ischemnia. A patient undergoing carotid endarterectomy specifically or other cerebrovascular or vascular surgical procedures in general, or diagnostic vascular procedures including cerebral angiography and the like.

Other incidents are head trauma, spinal cord trauma, or injury from general anoxia, hypoxia, hypoglycemia, hypotension as well as similar injuries seen during procedures from embole, hyperfusion, and hypoxia.

The instant invention would be useful in a range of incidents, for example, during cardiac bypass surgery, in incidents of intracranial hemorrhage, in perinatal asphyxia, in cardiac arrest, and status epilepticus.

Pain refers to acute as well as chronic pain.

Acute pain is usually short-lived and is associated with hyperactivity of the sympathetic nervous system. Examples are postoperative pain and allodynia.

Chronic pain is usually defined as pain persisting from 3 to 6 months and includes somatogenic pains and psychogenic pains. Other pain is nociceptive.

Still other pain is caused by injury or infection of peripheral sensory nerves. It includes, but is not limited to pain from peripheral nerve trauma, herpes virus infection, diabetes mellitus, causalgia, plexus avulsion, neuroma, limb amputation, and vasculitis. Neuropathic pain is also caused by nerve damage from chronic-alcoholism, human immunodeficiency virus infection, hypothyroidism, uremia, or vitamin deficiencies. Neuropathic pain includes, but is not limited to pain caused by nerve injury such as, for example, the pain diabetics suffer from.

Psychogenic pain is that which occurs without an organic origin such as low back pain, atypical facial pain, and chronic headache.

Other types of pain are: inflammatory pain, osteoarthritic pain, trigeminal neuralgia, cancer pain, diabetic neuropathy, restless leg syndrome, acute herpetic and postherpetic neuralgia, causalgia, brachial plexus avulsion, occipital neuralgia, gout, phantom limb, burn, and other forms of neuralgia, neuropathic and idiopathic pain syndrome.

A skilled physician will be able to determine the appropriate situation in which subjects are susceptible to or at risk of, for example, stroke as well as suffering from stroke for administration by methods of the present invention.

The compounds of the invention are also expected to be useful in the treatment of depression. Depression can be the result of organic disease, secondary to stress associated with personal loss, or idiopathic in origin. There is a strong tendency for familial occurrence of some forms of depression suggesting a mechanistic cause for at least some forms of depression. The diagnosis of depression is made primarily by quantification of alterations in patients' mood. These evaluations of mood are generally performed by a physician or quantified by a neuropsychologist using validated rating scales, such as the Hamilton Depression Rating Scale or the Brief Psychiatric Rating Scale. Numerous other scales have been developed to quantify and measure the degree of mood alterations in patients with depression, such as insomnia, difficulty with concentration, lack of energy, feelings of worthlessness, and guilt. The standards for diagnosis of depression as well as all psychiatric diagnoses are collected in the Diagnostic and Statistical Manual of Mental Disorders (Fourth Edition) referred to as the DSM-IV-R manual published by the American Psychiatric Association, 1994.

GABA is an inhibitory neurotransmitter with the central nervous system. Within the general context of inhibition, it seems likely that GABA-mimetics might decrease or inhibit cerebral function and might therefore slow function and decrease mood leading to depression.

The compounds of the instant invention may produce an anticonvulsant effect through the increase of newly created GABA at the synaptic junction. If gabapentin does indeed increase GABA levels or the effectiveness of GABA at the synaptic junction, then it could be classified as a GABA-mimetic and might decrease or inhibit cerebral function and might, therefore, slow function and decrease mood leading to depression.

The fact that a GABA agonist or GABA-mimetic might work just the opposite way by increasing mood and thus, be an antidepressant, is a new concept, different from the prevailing opinion of GABA activity heretofore.

The compounds of the instant invention are also expected to be useful in the treatment of anxiety and of panic as demonstrated by means of standard pharmacological procedures.

MATERIAL AND METHODS

Carrageenin-induced Hyperalgesia

Nociceptive pressure thresholds were measured in the rat paw pressure test using an analgesimeter (Randall-Selitto method: Randall L. O. and Selitto J. J., "A method for measurement of analgesic activity on inflamed tissue," Arch. Int. Pharmacodyn., 1957;4:409–419). Male Sprague-Dawley rats (70–90 g) were trained on this apparatus before the test day. Pressure was gradually applied to the hind paw of each rat and nociceptive thresholds were determined as the pressure (g) required to elicit paw withdrawal. A cutoff point of 250 g was used to prevent any tissue damage to the paw. On the test day, two to three baseline measurements were taken before animals were administered 100 µL of 2% carrageenin by intraplantar injection into the right hind paw. Nociceptive thresholds were taken again 3 hours after carrageenin to establish that animals were exhibiting hyperalgesia. Animals were dosed with either gabapentin (3–300 mg, s.c.), morphine (3 mg/kg, s.c.) or saline at 3.5 hours after carrageenin and nociceptive thresholds were examined at 4, 4.5, and 5 hours postcarrageenin.

(R)-2-Aza-spiro[4.5]decane-4-carboxylic acid hydrochloride was tested in the above carrageenan-induced hyperalgesia model. The compound was dosed orally at 30 mg/kg, and 1 hour postdose gave a percent of maximum possible effect (MPE) of 53%. At 2 hours postdose, it gave only 4.6% of MPE.

Semicarbazide-induced Tonic Seizures

Tonic seizures in mice are induced by subcutaneous administration of semicarbazide (750 mg/kg). The latency to the tonic extension of forepaws is noted. Any mice not convulsing within 2 hours after semicarbazide are considered protected and given a maximum latency score of 120 minutes.

Animals

Male Hooded Lister rats (200–250 g) are obtained from Interfauna (Huntingdon, UK) and male TO mice (20–25 g) are obtained from Bantin and Kingman (Hull, UK). Both rodent species are housed in groups of six. Ten Common Marmosets (Callithrix Jacchus) weighing between 280 and 360 g, bred at Manchester University Medical School (Manchester, UK) are housed in pairs. All animals are housed under a 12-hour light/dark cycle (lights on at 07.00 hour) and with food and water ad libitum.

Drug Administration

Drugs are administered either intraperitoneally (IP) or subcutaneously (SC) 40 minutes before the test in a volume of 1 mL/kg for rats and marmosets and 10 mL/kg for mice.

Mouse Light/Dark Box

The apparatus is an open-topped box, 45 cm long, 27 cm wide, and 27 cm high, divided into a small (2/5) and a large (3/5) area by a partition that extended 20 cm above the walls (Costall B., et at., "Exploration of mice in a black and white box: validation as a model of anxiety," *Pharmacol. Biochem. Behav.*, 1989;32:777–785).

There is a 7.5×7.5 cm opening in the center of the partition at floor level. The small compartment is painted black and the large compartment white. The white compartment is illuminated by a 60-W tungsten bulb. The laboratory is illuminated by red light. Each mouse is tested by placing it in the center of the white area and allowing it to explore the novel environment for 5 minutes. The time spent in the illuminated side is measured (Kilfoil T., et al., "Effects of anxiolytic and anxiogenic drugs on exploratory activity in a simple model of anxiety in mice," Neuropharmacol., 1989;28:901–905).

Rat Elevated X-Maze

A standard elevated X-maze (Handley S. L., et al., "Effects of alpha-adrenoceptor agonists and antagonists in a maze-exploration model of 'fear'-motivated behavior," *NaunynSchiedeberg's Arch. Pharmacol.*, 1984;327:1–5), was automated as previously described (Field, et al., "Automation of the rat elevated X-maze test of anxiety," *Br. J. Pharmacol.*, 1991;102(Suppl.):304P). The animals are placed on the center of the X-maze facing one of the open arms. For determining anxiolytic effects the entries and time spent on the end half sections of the open arms is measured during the 5-minute test period (Costall, et al., "Use of the elevated plus maze to assess anxiolytic potential in the rat," *Br. J. Pharmacol.*, 1989;96(Suppl.):312p).

Marmoset Human Threat Test

The total number of body postures exhibited by the animal towards the threat stimulus (a human standing approximately 0.5 m away from the marmoset cage and staring into the eyes of the marmoset) is recorded during the 2-minute test period. The body postures scored are slit stares, tail postures, scent marking of the cage/perches, piloerection, retreats, and arching of the back. Each animal is exposed to the threat stimulus twice on the test day before and after drug treatment The difference between the two scores is analyzed using one-way analysis of variance followed by Dunnett's t-test. All drug treatments are carried out SC at least 2 hours after the first (control) threat. The pretreatment time for each compound is 40 minutes.

Rat Conflict Test

Rats are trained to press levers for food reward in operant chambers. The schedule consists of alternations of four 4-minute unpunished periods on variable interval of 30 seconds signaled by chamber lights on and three 3-minute punished periods on fixed ratio 5 (by footshock concomitant to food delivery) signaled by chamber lights off. The degree of footshock is adjusted for each rat to obtain approximately 80% to 90% suppression of responding in comparison with unpunished responding. Rats receive saline vehicle on training days.

DBA2 Mouse Model of Anticonvulsant Efficacy

All procedures were carried out in compliance with the NIH Guide for the Care and Use of Laboratory Animals under a protocol approved by the Parke-Davis Animal Use Committee. Male DBA/2 mice, 3 to 4 weeks old were obtained from Jackson Laboratories, Bar Harbour, Me. Immediately before anticonvulsant testing, mice were placed upon a wire mesh, 4 inches square, suspended from a steel rod. The square was slowly inverted through 180° and mice observed for 30 seconds. Any mouse falling from the wire mesh was scored as ataxic (Coughenour L. L., McLean J. R., Parker R. B., "A new device for the rapid measurement of impaired motor function in mice," *Pharm. Biochem. Behav.*, 1977;6(3):351–3). Mice were placed into an enclosed acrylic plastic chamber (21 cm height, approximately 30 cm diameter) with a high-frequency speaker (4 cm diameter) in the center of the top lid. An audio signal generator (Protek model B-810) was used to produce a continuous sinusoidal tone that was swept linearly in frequency between 8 kHz and 16 kHz once each 10 msec. The average sound pressure level (SPL) during stimulation was approximately 100 dB at the floor of the chamber. Mice were placed within the chamber and allowed to acclimatize for one minute. DBA/2 mice in the vehicle-treated group responded to the sound stimulus (applied until tonic extension occurred, or for a maximum of 60 sec) with a characteristic seizure sequence consisting of wild running followed by clonic seizures, and later by tonic extension, and finally by respiratory arrest and death in 80% or more of the mice. In vehicle-treated mice, the entire sequence of seizures to respiratory arrest lasts approximately 15 to 20 seconds. The incidence of all the seizure phases in the drug-treated and vehicle-treated mice was recorded, and the occurrence of tonic seizures were used for calculating anticonvulsant $ED_{50}$ values by probit analysis (Litchfield J. T., Wilcoxon F. "A simplified method for evaluating dose-effect experiments," *J. Pharmacol.*, 1949;96:99–113). Mice were used only once for testing at each dose point. Groups of DBA/2 mice (n=5–10 per dose) were tested for sound-induced seizure responses 2 hours (previously determined time of peak effect) after given drug orally. All drugs in the present study were dissolved in distilled water and given by oral gavage in a volume of 10 mL/kg of body weight. Compounds that are insoluble will be suspended in 1% carboxymethocellulose. Doses are expressed as weight of the active drug moiety.

The compounds of the instant invention are also expected to be useful in the treatment of pain and phobic disorders (*Am. J. Pain Manag.*, 1995;5:7–9).

The compounds of the instant invention are also expected to be useful in treating the symptoms of manic, acute or chronic, single upside, or recurring depression. They are also expected to be useful in treating and/or preventing bipolar disorder (U.S. Pat. No. 5,510,381).

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or synthetic guns, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsules, tablet, cachet, or lozenge itself, or it can be the appropriate number of any of these in packaged form.

The quantity of active component in a unit dose preparation may be varied or adjusted from 0.1 mg to 1 g according to the particular application and the potency of the active component. In medical use the drug may be administered three times daily as, for example, capsules of 100 or 300 mg. The composition can, if desired, also contain other compatible therapeutic agents.

In therapeutic use, the compounds utilized in the pharmaceutical method of this invention are administered at the initial dosage of about 0.01 mg to about 100 mg/kg daily. A daily dose range of about 0.01 mg to about 100 mg/kg is preferred. The dosages, however, may be varied depending upon the requirements of the patient, the severity of the condition being treated, and the compound being employed Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

The following examples are illustrative of the instant invention; they are not intended to limit the scope.

EXAMPLE 1

(±)-(1α,6β)(2-Aminomethyl-octahydro-inden-2-yl)-acetic Acid Hydrochloride

Step (i)

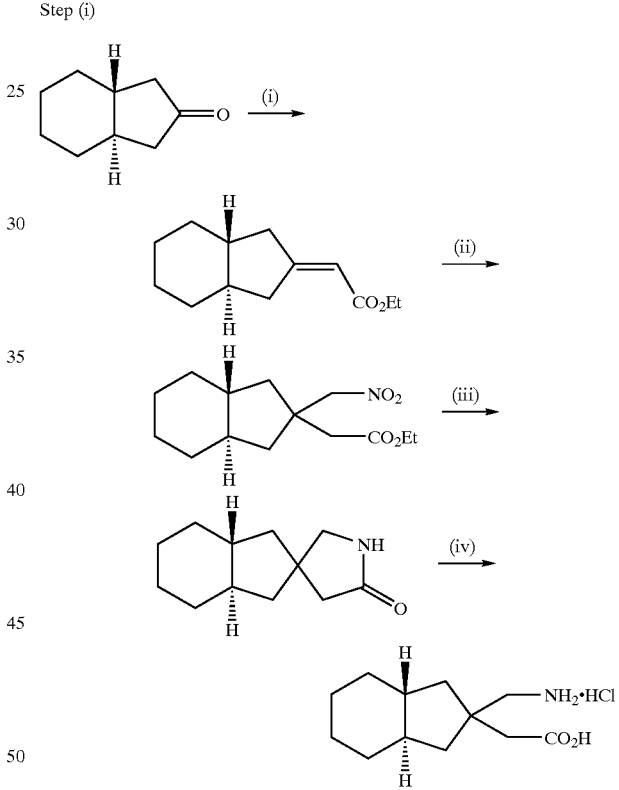

Sodium hydride (0.11 mg, 2.7 mmol) was stirred with THF (5 mL) at 0° C. under argon. Triethylphosphonoacetate (0.5 mL) was added dropwise and the solution stirred for 10 minutes. The ketone (0.37 g, 7.7 mmol) in THF (5 mL) was added dropwise with stirring and left to warm to room temperature. After 18 hours, the reaction mixture was separated between water (80 mL) and diethyl ether (3×20 mL). Solvent was removed in vacuo to give a yellow oil, which was purified via flash chromatography (silica, heptane/EtOAC 19:1). To give 0.34 g (62%) of the ester as a colorless oil:

$^1$H NMR (CDCl$_3$) (400 MHz): 1.05–1.29 (9H, m, ring protons+CH$_3$), 1.76–1.78 (2H, m, ring protons), 1.87–1.97 (2H, m, ring protons), 2.0–2.16 (2H, m, ring protons), 2.51–2.56 (1H, dd, J=5.7, 27.5 Hz, ring protons), 3.12–3.18 (1H, dd, J=5.4, 18.8 Hz, ring protons), 4.12–4.20 (2H, m, CH$_2$), 5.77 (1H, s, CH). MS (ES$^+$) m/e 209 [M+H]$^+$ 100%.

Step (ii)

Ester (0.34 g, 1.63 mmol) was dissolved in THF (5 mL), with stirring under argon. Nitromethane (0.25 mL) was added and the reaction mixture heated to 60° C. TBAF (2.3 mL) was added dropwise to the hot solution over 1 hour and stirred for 4 hours. The reaction mixture was partitioned between 2N HCl and diethyl ether, and the diethyl ether layer was washed with brine. Solvent was removed in vacuo to give a yellow oil, which was purified via flash chromatography (silica, heptane/EtOAC, 19:1), to give 0.264 g (60%) of the product as a colorless oil.

$^1$H NMR (CDCl$_3$)(400 MHz): δ 0.97–1.30 (11H, m, ring protons+CH$_3$), 1.73–1.95 (6H, m, 2×CH+4 ring protons), 2.5 (1H, d, J=16.6 Hz, CH$_2$CO$_2$Et), 2.7 (1H, d, J=16.6 Hz, CH$_2$CO$_2$Et), 4.12–4.18 (2H, m CH$_2$), 4.49–4.51 (1H, d, J=11.5 Hz, CH$_2$NO$_2$), 4.73–4.75 (1H, d, J=11.5 Hz, CH$_2$NO$_2$).

Step (iii)

Nitroester (0.24 g, 0.9 mmol) was dissolved in methanol with Nickel sponge. Reaction was hydrogenated at 50 psi, 30° C. for 15 hours. The reaction mixture was filtered through celite, and the solvent removed in vacuo to give the product 0.18 g (85%) as a yellow solid. This product was a mixture of lactam and amino ester.

Step (iv)

Amino ester was taken up in 6N HCl (5 mL) and dioxane (2.5 mL), and heated to reflux for 4 hours. The solution was washed with dichloromethane (3×5 mL), and the aqueous fraction was evaporated in vacuo to give 0.196 g (99%) of product as a colorless solid.

$^1$H NMR (DMSO)(400 MHz): δ 0.86–1.04 (2H, m), 1.08–1.17 (6H, m), 1.60–1.78 (6H, m), 2.35–2.39 (1H, d, J=16 Hz, CH$_2$CO$_2$H), 2.46 (1H, m, CH$_2$CO$_2$H), 2.83–2.87 (1H, d, J=13 Hz, CH$_2$NH$_2$), 2.97–3.00 (1H, d, J=13 CH$_2$NH$_2$), 7.91 (2H, bs, NH$_2$). MS (ES$^+$) m/e 212 [M+H$^+$ 100%. HPLC, Prodigy C18 column, 5% methanol/acetonitrile. Retention time=3.00 minutes, and a purity of 99%.

EXAMPLE 2

(±)-(1α,5β)(2-Aminomethyl-octahydro-pentalen-2-yl)-acetic Acid Hydrochloride

Step (i)

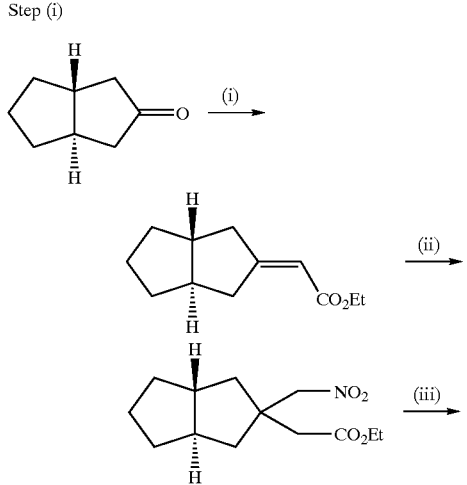

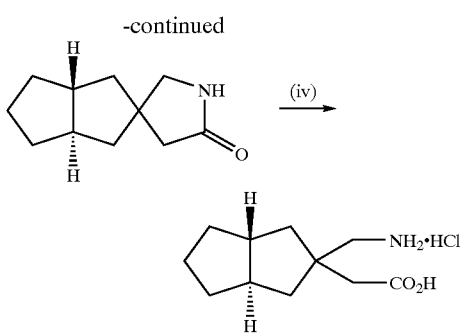

Sodium hydride (0.6 g, 14.5 mmol) was stirred with THF (50 mL) at 0° C. under argon. Triethylphosphonoacetate (2.9 mL) was added dropwise and the solution stirred for 10 minutes. The ketone (1.8 g, 14.5 mmol) in THF (10 mL) was added dropwise with stirring and left to warm to room temperature. After 18 hours, the reaction mixture was separated between water (250 mL) and diethyl ether (3×50 mL). Solvent was removed in vacuo to give a yellow oil, which was purified via flash chromatography (silica, heptane/EtOAC 19:1). To give 1.95 g (69%) of the ester was a colorless oil:

$^1$H NMR (CDCl$_3$)(400 MHz): δ 1.14–1.19 (2H, m, CH$_2$), 1.25–1.29 (3H, m, CH$_3$), 1.55–1.79 (4H, m, 2×CH$_2$), 2.03–2.10 (4H, m, 2×CH$_2$), 2.45–2.55 (1H dd, CH), 3.05–3.15 (1H, dd, CH), 4.12–4.17 (2H, q, J=7.3, 14.4 Hz, COCH$_2$), 5.76 (1H, m, CH).

Step (ii)

Ester (1.9 g, 10 mmol) was dissolved in THF (15 mL), with stirring under argon. Nitromethane (1.4 mL) was added, and the reaction mixture heated to 60° C. TBAF (14 mL) was added dropwise to the hot solution over 1 hour, and stirred for hours. The reaction mixture was separated between 2N HCl and diethyl ether, and then the ether layer was washed with brine. Diethyl ether was removed in vacuo to give an orange oil, which was purified via flash chromatography (silica, heptane/EtOAC, 19:1), to give 1.59 g (64%) of the product as a colorless oil.

$^1$H NMR (CDCl$_3$)(400 MHz): δ 1.14–1.31 (7H, m, CH$_3$+ring protons), 1.64–1.72 (5H, m, ring protons), 1.03–1.09 (1H, m, ring protons), 2.00–2.05 (2H, m, ring protons), 2.57–2.61 (1H, d, J=16.4 Hz, CH$_2$CO$_2$Et), 2.71–2.75 (1H, d, J=16.4 Hz, CH$_2$CO$_2$Et), 4.124.18 (2H, q, J=7.1, 14.2 Hz, OCH$_2$CH$_3$), 4.56–4.59 (1H, d, J=11.5 Hz, CH$_2$NO$_2$), 4.774.80 (1H, d, J=11.5 Hz, CH$_2$NO$_2$). IR (neat) 2957, 2870, 1731, 1547, 1374, 1182, 1030cm$^{-1}$.

Step (iii)

Nitroester (1.59 g, 5.9 mmol) was dissolved in methanol (40 mL) with Nickel sponge. Reaction was hydrogenated at 50 psi, 30° C. for 5 hours. The reaction mixture was filtered through celite, and the solvent removed in vacuo to give the lactam 1.08 g (97%) as an off-white solid.

$^1$H NMR (CDCl$_3$)(400 MHz): δ 1.08–1.11 (2H, m, ring protons), 1.23–1.28 (2H, m, ring protons), 1.62–1.68 (4H, m), 1.82–1.89 (2H, m), 2.00–2.06 (2H, m), 2.30–2.40 (2H, m, CH$_2$CO), 3.29–3.30 (2H, M, CH$_2$NH), 5.45 (1H, bs, NH). MS (ES$^+$) m/e 180 [M+H]$^+$ 3%, 359 [2M+H]$^+$ 21%, 381 2M+Na]$^+$ 100%.

Step (iv)

Lactam was taken up in 6N HCl (20 mL) and dioxane (8 mL), and heated to reflux for 4 hours. The solution was washed with dichloromethane (3×10 mL), and the aqueous fraction was evaporated in vacuo to give 0.65 g (84%) of product as a colorless solid.

¹H NMR (DMSO) (400 MHz): δ 1.0–1.18 (4H, m, ring protons), 1.52–1.72 (6H, m, ring protons), 1.95–2.02 (2H, m, ring protons), 2.33–2.67 (2H, m, CH₂CO₂H), 2.90–2.94 (1H, d, J=12.9 Hz, CH₂NH₂), 3.00–3.03 (1H, d, J=12.7 Hz, CH₂NH₂), 7.94 (2H, bs, NH₂). MS (ES⁺) m/e 198 [M+H]⁺ 100%. LCMS (ELSD) Prodigy ODS3 50 mm×2 mm column, 5%–50% MeCN/H₂O. Retention time=2.30 minutes, mass found=198. 100% purity.

EXAMPLE 3

(1α,3α,5α)(2-Aminomethyl-octahydro-pentalen-2-yl)-acetic Acid Hydrochloride

Step (i)

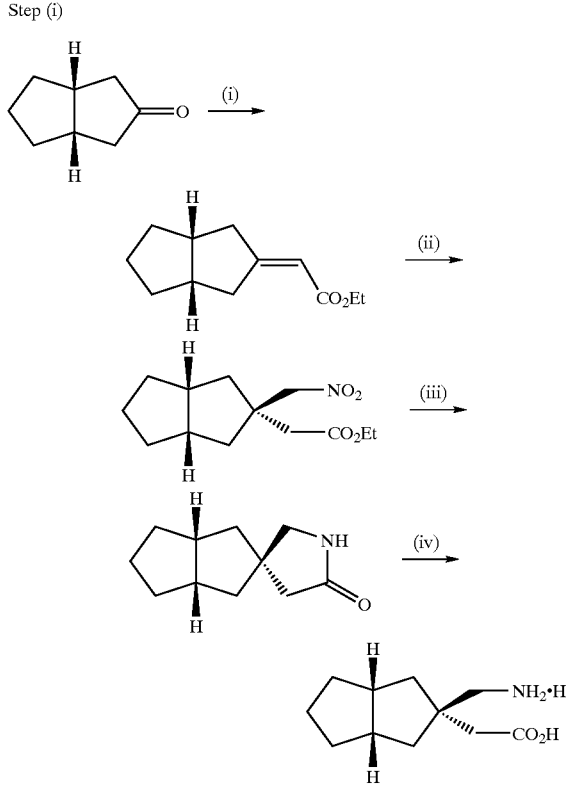

To a suspension of NaH (0.45 g, 11.3 mmol) in THF (25 mL), at 0° C. under argon, was slowly added (over ~10 minutes) triethylphosphonoacetate (2.3 mL, 11.6 mmol), followed by 5 (1.29 g, 10.4 mmol in 2×3 mL THF). The reaction was allowed to warm to room temperature and left to stir for 4 hours, after which it was diluted with water (100 mL), extracted with ether (2×200 mL), washed with saturated brine (50 mL), and dried (MgSO₄). Column chromatography (9:1 heptane/ethyl acetate) gave the product as a colorless oil, 1.75 g, 86%.

IR(thin film)(cm⁻¹) ν=2964, 1713, 1655, 1371, 1208, 1125, 1040. ¹H NMR (CDCl₃): δ 5.72 (1H, m), 4.14 (2H, q, J=7.2), 3.02–2.92 (1H, m), 2.72–2.54 (3H, m), 2.52–2.42 (1H, m), 2.28–2.20 (1H, m), 1.85–1.31 (6H, m), 1.27 (3H, t, J=7.2). m/z AP⁺ 195 (MI+1) at 100%.

Step (ii)

To a solution of 6 (2.75 g, 22.2 mmol) in THF (22 mL) was added TBAF (24 mL, 24.0 mmol) followed by nitromethane (4.4 mL, 8.14 mmol). The reaction was heated (oil bath at 60° C.) for 4.75 hours, after which it was diluted with ethyl acetate (100 mL) and washed with 2M HCl (30 mL), followed by saturated brine (40 mL), dried (MgSO₄), and concentrated under reduced pressure. Column chromatography (9:1 heptane/ethyl acetate) gave the product as a colorless oil, 0.73 g, 20%. The product was found by 1H NMR to be a 9:1 mixture of diastereoisomers.

¹H NMR (CDCl₃): δ 4.67 (1H, s), 4.60 (1H, s), 4.15 (2H, q, J=7.2), 4.14 (2H, q, 7.2), 2.58 (2H, s), 2.49 (2H, s), 2.12–2.0 (2H+2H, m), 1.63–1.49 (4H+4H, m) 1.44–1.36 (2H+2H, m) 1.28 (3H, t, J=7.2), 1.27 (3H, t, J=7) 1.16–1.04 (2H+2H, m).

Step (iii)

Compound 7 (0.88 g, 3.45 mmol) in methanol (100 mL) with nickel sponge catalyst underwent hydrogenation at 30° C. and a pressure of 56 psi; this was left for 5 hours. Before use, the nickel sponge catalyst was washed several times, first with water and then methanol. After hydrogenation was complete, the reaction mixture was filtered through celite and the resulting solution concentrated in vacuo to give a yellow solid, 0.62 g, 80%.

¹H NMR (CDCl₃): δ 5.43 (1H, br s), 3.15 (2H, s), 2.56–2.44 (3H, m), 1.99 (2H, dd, J=12.6, 8.2), 1.64–1.50 (2H, m), 1.44–1.34 (3H, m), 1.22–1.14 (2H, m). m/z ES⁺ 226 (MI+1) at 100%.

Step (iv)

Compound 8 (0.61 g, 2.7 mmol) in dioxane (10 mL) and 6 M HCl (30 mL) was heated to reflux (oil bath at 100° C.) for 4 hours. After cooling, the reaction was diluted with water (40 mL) and the reaction mixture washed with dichloromethane (3×40 mL) and concentrated in vacuo to yield a white crystalline product as a 6:1 ratio of diastereoisomers. The product was recrystallized twice from ethyl acetate/methanol to give a 10:1 mixture of diastereoisomers.

m/z ES⁺ 198 (MI+1) at 100%. ¹H NMR (D₂O): δ 3.03 (2H, s), 2.50–2.36 (4H, m), 1.84 (2H, dd, J=12.8), 1.41 (4H, 1.26 (2H, s), 1.02 (2H, m). HPLC column=Prodigy ODS 3, room temperature=0.87, Purity=100%.

EXAMPLE 4

(1α,6α,8α)(2-Aminomethyl-octahydro-inden-2-yl)-acetic Acid Hydrochloride

Synthesis of compound 1

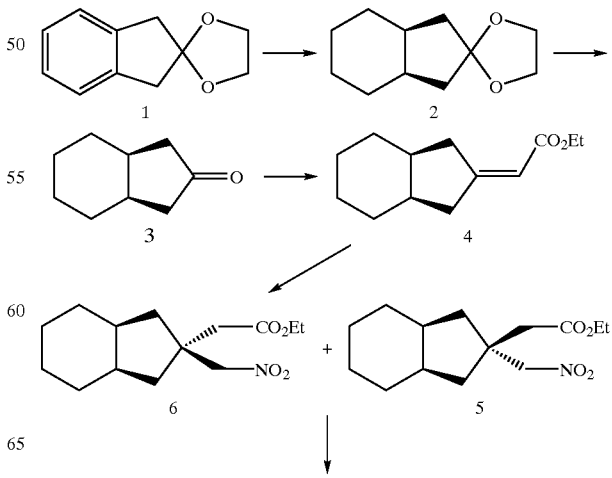

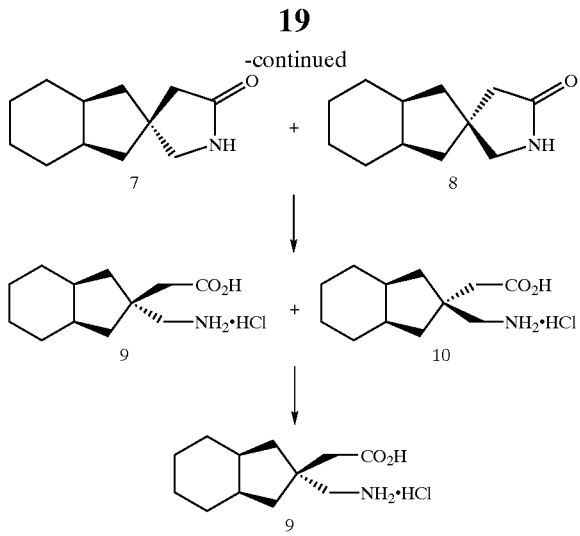

Indan-2-one (1.0 g, 7.6 mmol), ethylene glycol (0.43 mL, 7.6 mmol), and paratoluene sulphonic acid were refluxed in benzene (40 ml) using a Dean-Stark trap for 6 hours. The mixture was allowed to cool and was then diluted with ethyl acetate (100 mL) and washed with saturated sodium hydrogen carbonate solution (60 mL). The organic layer was separated off, and the aqueous layer was extracted further with ethyl acetate (2×50 mL). The combined organic fractions were washed with brine, dried ($MgSO_4$), and the solvent was evaporated under reduced pressure. The residue was chromatographed ($SiO_2$, heptane/ethyl acetate, 97:3) to give the acetal 1 (1.14 g, 85%) as a colorless oil; $R_f$(heptane/ethyl acetate, 8:2) 0.36; $v_{max}$(film)/$cm^{-1}$ 1483, 1331, 1291, 1105; $\delta_H$ (400 MHz; $CDCl_3$): 7.19–7.14 (4H, m, Ph), 4.02 (4H, s, 2×$CH_2CO_2$), 3.18 (4H, s, 2×$CH_2O$).

Synthesis of Compound 2

Acetal 1 (0.5 g, 2.84 mmol) in ethanol (50 mL) was shaken over a catalytic amount of 5% rhodium on alumina under a hydrogen atmosphere (70 Psi, 50° C.) for 16 hours. The catalyst was filtered off, and the solvent was evaporated under reduced pressure to give the acetal 2 (0.51 g, 99%) as a colorless oil; $v_{max}$(film)/$cm^{-1}$ 2923, 1449, 1337, 1192, 1115, 1089; $\delta_H$ (400 MHz; $CDCl_3$): 3.89–3.86 (4H, m, 2×$CH_2O$), 2.10–2.00 (2H, m), 1.88 (2H, dd, J=13.9, 7.6), 1.81 (2H, dd, J=13.7, 7.0), 1.56–1.26 (6H, m).

Synthesis of Compound 3

Acetal 2 (1.01 g, 5.54 mmol) was stirred in a mixture of 2N hydrochloric acid (10 mL) and acetone (10 mL) for 24 hours. After this time, tlc showed complete consumption of the starting acetal. Saturated sodium carbonate solution (20 mL) was added, and the mixture was extracted with ether (3×25 mL). The combined ether fractions were washed with brine, dried ($MgSO_4$), and the solvent was evaporated under reduced pressure. The residue was chromatographed ($SiO_2$, pentane/ether, 95:5) to give the ketone 3 (0.75 g, 97%) as a colorless oil; $R_f$(heptane/ethyl acetate, 8:2) 0.42; $v_{max}$(film)/$cm^{-1}$ 1743 (C=O); $\delta_H$ (400 MHz; $CDCl_3$): 2.37–2.28 (2H, m), 2.20 (2H, dd, J=18.5, 7.5), 2.12 (2H, dd, J=18.7, 6.3), 1.65–1.24 (10H, m).

Synthesis of Compound 4

Triethyl phosphonoacetate (1.13 mL, 5.70 mmol) was added dropwise to a stirring suspension of sodium hydride (0.22 g of a 60% dispersion in oil, 5.43 mmol) in THF (15 mL) at 0° C. under argon. After 20 minutes, ketone 3 (0.75 g, 5.43 mmol) in THF (6 mL) was added dropwise. The mixture was allowed to warm to room temperature and stirred for 16 hours. Water (5 mL) was added, and the mixture was extracted with ether (15 mL×3). The combined organic fractions were washed with brine and dried ($MgSO_4$). The solvent was evaporated under reduced pressure. The residue was chromatographed ($SiO_2$, heptane/ethyl acetate, 95:5) to give the ester 4 (0.81 g, 72%) as a colorless oil; $R_f$heptane/ethyl acetate, 8:2) 0.66; $v_{max}$(film)/$cm^{-1}$ 1715 (C=O), 1652 (C=C); $\delta_H$ (400 MHz; $CDCl_3$): 5.80 (1H, quin, J=2.2, $CHCO_2Et$), 4.15 (2H, q, J=7.1, $CO_2CH_2Me$), 2.79 (1H, dd, J=19.5, 8.1), 2.69 (1H, ddt, J=19.8, 7.3, 2.3), 2.47 (1H, dd, J=17.3, 7.2), 2.34 (1H, ddt, J=17.3, 5.6, 1.8), 2.14 (1H, m), 2.02 (1H, m), 1.60–1.22 (8H, m); m/z ($ES^+$) 209 (M+H, 57%), 455 (2M+K, 67).

Synthesis of Compounds 5 and 6

Ester 4 (0.45 g, 2.16 mmol), nitromethane (0.24 mL, 4.31 mmol), and tetra-butylammonium fluoride (3.10 mmol of a 1 M solution in THF, 3.10 mmol) were heated to 65° C. in THF for 4 hours. The mixture was allowed to cool, diluted with ethyl acetate (20 mL), and acidified with dilute hydrochloric acid (15 mL). The organic layer was separated off, and the aqueous layer was further extracted with ethyl acetate (2×15 mL). The combined organic fractions were washed with brine, dried ($MgSO_4$), and the solvent was evaporated under reduced pressure. The residue was chromatographed ($SiO_2$, heptane/ethyl acetate, 98:2) to give a 9:1 ratio of nitro-esters 5 and 6 (0.35 g, 60%) as a yellow oil; $R_f$(heptane/ethyl acetate, 9:1) 0.28; $v_{max}$(film)/$cm^{-1}$ 1732 (C=O), 1547 ($NO_2$), 1375 ($NO_2$); major isomer 5: $\delta_H$ (400 MHz; $CDCl_3$): 4.61 (2H, s, $CH_2NO_2$), 4.15 (2H, q, J=7.2, $OCH_2Me$), 2.70 (2H, s, $CH_2CO_2Et$), 2.06 (2H, m), 1.81 (2H, dd, J=13.9, 7.1), 1.56 (2H, dd, J=13.1, 6.8), 1.51–1.22 (8H, m) 1.28 (3H, t, J=7.2).

Synthesis of Compounds 7 and 8

The mixture of 5 and 6 (0.81 g, 3.01 mmol) in methanol (30 mL) was shaken over a catalytic amount of nickel sponge catalyst under a hydrogen atmosphere (50 Psi, 30° C.) for 12 hours. The mixture was filtered, and the solvent was evaporated under reduced pressure to give a 9:1 mixture of aminoesters 7 and 8 (0.42 g, 72%) as a white solid; $v_{max}$(film)/$cm^{-1}$ 3214 (NH), 1706 (C=O); major isomer 7: $\delta_H$ (400 MHz; $CDCl_3$): 5.57 (1H, br s, NH), 3.20 (2H, s, $CH_2NH$), 2.36 (2H, s $CH_2CO$), 2.04–1.94 (2H, m), 1.77 (2H, dd, J=13.2, 7.0), 1.62 (2H, dd, J=13.4, 6.7), 1.60–1.20 (8H, m); m/z ($ES^+$) 387 (2M+H, 97%).

Synthesis of Compounds 9 and 10 and Resolution of Compound 9

(1α,6α,8α)(2-Aminomethyl-octahydro-inden-2-yl)-acetic acid hydrochloride The mixture of 7 and 8 (0.42 g, 2.17 mmol) was dissolved in 1,4-dioxane (8 mL) and hydrochloric acid (20 mL of a 6N solution), and the mixture was refluxed for 6 hours. After cooling, the mixture was diluted with water (20 mL) and washed with dichloromethane (2×15 mL). The aqueous layer was evaporated under reduced pressure to give a 9:1 mixture of acids 9 and 10 (0.43 g, 79%) as a white solid. Recrystallization using ethyl acetate/methanol gave acid 9 exclusively (0.27 g); $\delta_H$ (400 MHz; $d_6$-DMSO): 12.3 (1H, br s, $CO_2H$), 7.94 (2H, br s, NH2), 2.90 (2H, s, $CH_2NH_2$),2.52 (2H, s, $CH_2CO_2H$), 1.97 (2H, br s), 1.65 (2H, dd, J=13.5, 6.7), 1.54–1.20 (10H, m); m/z ($ES^+$) 212 (M+H, 100%); (Found: C, 56.4; H, 8.74; N, 5.43 $C_{12}H_{21}NO_2 \cdot 1HCl$. $0.5H_2O$ requires C, 56.1; H, 9.03; N 5.45%); LCMS (Prodigy C18 50 mm×4.6 mmid column, 5%–50% Acetonitrile/water); Retention Time=1.53 minutes, 98% purity.

EXAMPLE 5

((1α,6α,8β)(2-Aminomethyl-octahydro-inden-2-yl)-acetic Acid Hydrochloride

Synthesis of compound 1

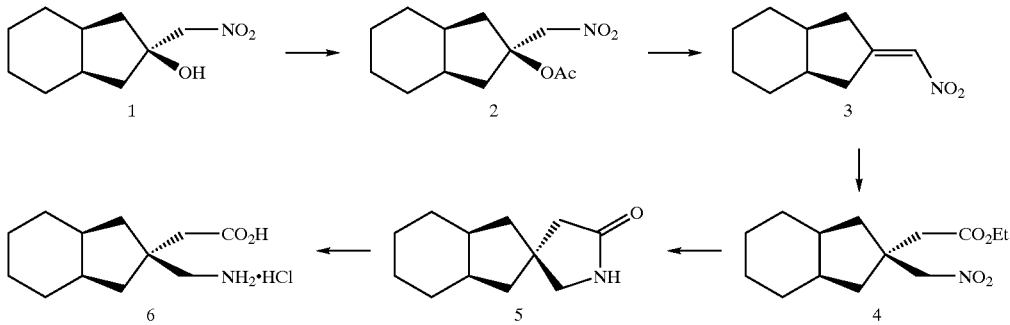

n-Butyllithium (5.1 mL of a 2.5 M solution in hexanes, 12.75 mmol) was added dropwise to a stirring mixture of nitromethane (0.34 mL, 6.3 mmol) in TBF (20 mL) and HMPA (2 mL) at −78° C. under argon. The mixture was allowed to warm to −60° C. and stirred for 1 hour. The mixture was cooled to −78° C. and 3 (0.79 g, 5.73 mmol) was added. The mixture was allowed to warm to −60° C. and stirred for a further 2 hours. The mixture was quenched by addition of saturated ammonium chloride solution (5 mL). After warming to room temperature, dilute hydrochloric acid (10 mL) and ether (30 mL) were added. The organic layer was separated, and the aqueous layer was further extracted with ether (2×25 mL). The combined organic fractions were washed with brine, dried (MgSO$_4$), and the solvent was evaporated under reduced pressure. The residue was chromatographed (SiO$_2$, heptane/ethyl acetate, 95:5) to give the nitro-alcohol 1 (0.50 g, 43%) as a white solid; R$_f$(heptane/ethyl acetate, 9:1) 0.14; ν$_{max}$(CH$_2$Cl$_2$)/cm$^{-1}$ 3424 (OH), 1548 (NO$_2$), 1379 (NO$_2$); δ$_H$ (400 MHz; CDCl$_3$): 4.45 (2H, s, CH$_2$NO$_2$), 3.26 (1H, s, OH), 2.04–1.95 (2H, m), 1.85–1.80 (4H, m), 1.64–1.24 (8H, m).

Synthesis of Compound 2

A mixture of 1 (0.50 g, 2.49 mmol) and concentrated sulphuric acid (1 drop) was heated to 50° C. in acetic anhydride (1 mL) for 5 minutes. The mixture was allowed to cool and then partitioned between ether (100 mL) and water (50 mL). The ether layer was washed with brine, dried (MgSO$_4$), and the solvent was evaporated under reduced pressure to give the nitroacetate 2 (0.49 g, 82%) as a colorless oil; R$_f$(heptane/ethyl acetate, 9:1) 0.44; ν$_{max}$(film)/cm$^{-1}$ 1739 (C=O), 1551 (NO$_2$), 1375 (NO$_2$); δ$_H$(400 MHz; CDCl$_3$): 4.88 (2H, s, CH$_2$NO$_2$), 2.38–2.00 (8H, m), 2.07 (3H, s, MeCO), 1.62–1.32 (6H, m).

Synthesis of Compound 3

Potassium methoxide (0.15 g, 2.04 mmol) in methanol (3 mL) was added dropwise to a stirring solution of 2 (0.49 g, 2.04 mmol) in methanol (5 mL) at 0° C. After 10 minutes, the mixture was partitioned between ether (100 mL) and water (50 mL). The ether layer was washed with brine, dried (MgSO$_4$) and the solvent was evaporated under reduced pressure. The residue was chromatographed (SiO$_2$, pentane/ether, 98:2) to give the nitro-alkene 3 (0.21 g, 57%) as a pale yellow oil; R$_f$(heptane/ethyl acetate, 8:2) 0.54; ν$_{max}$(film)/cm$^{-1}$ 1643 (C=C), 1509 (NO$_2$), 1342 (NO$_2$); δ$_H$(400 MHz; CDCl$_3$): 7.12 (1H, quin, J=2.0, CHNO$_2$), 3.01 (1H, ddt, J=20.5, 8.0, 2.1), 2.90 (1H, ddt, J=20.5, 7.3, 2.1), 2.54 (1H, ddt, J=17.8, 7.1, 2.0), 2.43 (1H, ddt, J 17.7, 5.6, 1.9), 2.21 (1H, m), 2.12 (1H, m), 1.60–1.24 (8H, m).

Synthesis of Compound 4

Ethyl acetate (0.12 mL, 1.22 mmol) in THF (2 mL) was added dropwise to a stirring solution of lithium bis (trimethylsilyl)amide (1.22 mL of a 1 M solution in THF, 1.22 mmol) at −78° C. under argon. After 20 minutes, 3 (0.21 g, 1.16 mmol) in THF (1 mL) was added, and the mixture was stirred for 2 hours. The mixture was quenched by addition of saturated ammonium chloride solution (3 mL) and allowed to warm to room temperature. The mixture was diluted with ether (20 mL) and dilute hydrochloric acid (15 mL) was added. The organic layer was separated, and the aqueous layer was further extracted with ether (2×10 mL). The combined organic fractions were washed with brine, dried (MgSO$_4$), and the solvent was evaporated under reduced pressure. The residue was chromatographed (SiO$_2$, heptane/ethyl acetate, 99:1) to give the nitro-ester 4 (0.13 g, 41%) as a colorless liquid; R$_f$(heptane/ethyl acetate, 9:1) 0.32; ν$_{max}$(film)/cm$^{-1}$ 1731 (C=O), 1547 (NO$_2$), 1375 (NO$_2$); δ$_H$(400 MHz; CDCl$_3$): 4.73 (2H, s, CH$_2$NO$_2$), 4.14 (2H, q, J=7.1, CO$_2$CH$_2$Me), 2.58 (2H, s, CH$_2$CO$_2$Et), 2.07 (2H, m), 1.71–1.66 (4H, m), 1.60–1.24 (8H, m), 1.26 (3H, t, J=7.2, CO$_2$CH$_2$Me); m/z (ES$^+$) 270 (M+H, 100%).

Synthesis of Compound 5

4 (0.122 g, 0.45 mmol) in methanol (40 mL) was shaken over a catalytic amount of nickel sponge catalyst under a hydrogen atmosphere (60 Psi, 30° C.) for 6 hours. The mixture was filtered and the solvent was evaporated under reduced pressure to give amino-ester 5 (0.084 g, 96%) as a white solid; ν$_{max}$(film)/cm$^{-1}$ 3228 (NH), 1665 (C=O); δ$_H$ (400 MHz; CDCl$_3$): 5.49 (1H, br s, NH), 3.34 (2H, s, CH$_2$NH), 2.25 (2H, s, CH$_2$CO), 2.10–1.98 (2H, m), 1.77 (2H, dd, J=13.2, 7.1), 1.65 (2H, dd, J=13.2, 6.8), 1.62–1.20 (8H, m).

Synthesis of Compound 6

(2-Aminomethyl-octahydro-inden-2-yl)-acetic acid 5 (0.083 g, 0.43 mmol) was dissolved in 1,4-dioxane (2 mL) and hydrochloric acid (8 mL of a 6N solution), and the mixture was refluxed for 5 hours. After cooling, the mixture was diluted with water (20 mL) and washed with dichloromethane (2×15 mL). The aqueous layer was evaporated under reduced pressure to give the acid 6 (0.097 g, 91%) as a white solid. This was recrystallized using ethyl acetate/methanol to give pure 10 (0.057 g); δ$_H$ (400 MHz; d$_6$-DMSO): 7.90 (2H, br s, NH$_2$), 3.02 (2H, s, CH$_2$NH$_2$), 2.43 (2H, s, CH$_2$CO$_2$H), 2.00 (2H, br s), 1.53–1.24 (12H, m); m/z (ES$^+$) 212 (M+H, 100%); LCMS (Prodigy C18 50 mm×4.6 mmid column, 5%–50% Acetonitrile/water) Retention Time=1.12 minutes, 100% purity.

EXAMPLE 6

(1α,3α,5α)(3-Aminomethyl-bicyclo[3.2.0]hept-3-yl)-acetic Acid Hydrochloride

Synthesis of compound 1

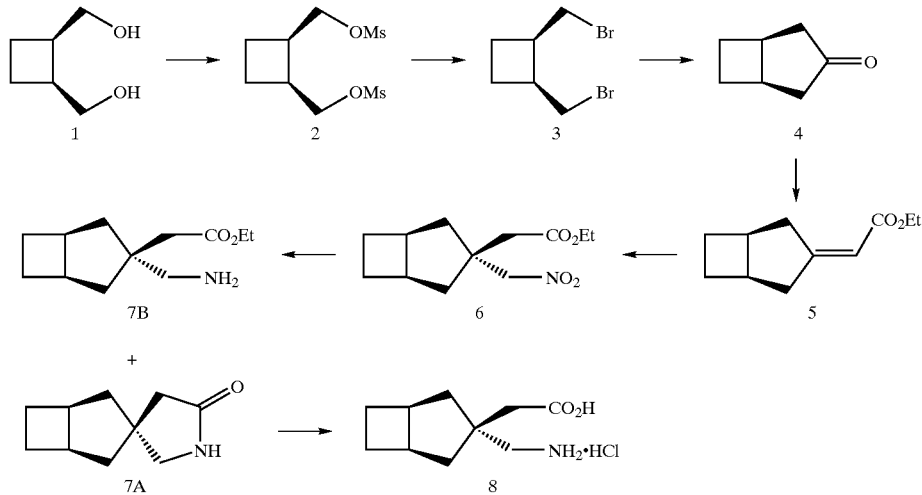

Lithium aluminum hydride (69.4 mL of a 1 M solution in ether, 69.4 mmol) was added dropwise to a stirring solution of cis-cyclobutane-1,2-dicarboxylic acid (5 g, 34.7 mmol) in THF (60 mL) at 0° C. under argon. The mixture was allowed to warm to room temperature and stirred for 16 hours. The mixture was cooled to 0° C. and quenched by careful addition of water (2.7 mL), sodium hydroxide solution (2.7 mL of a 15% w/v solution), and water (8.1 mL). The mixture was stirred for 15 minutes, and the precipitate was removed by filtration. The solvent was evaporated under reduced pressure to give the alcohol 1 as a colorless oil (4.0 g, 98%); $\delta_H$ (400 MHz; CDCl$_3$): 3.85 (2H, m), 3.6 (2H, m), 3.2 (2H, s), 2.7 (2H, m), 2 (2H, m); 1.55 (2H, m); $\delta_C$ (400 MHz; CDCl$_3$): 63.15, 37.83, 20.40.

Synthesis of Compound 2

Mesyl chloride (6.2 mL, 79.1 mmol) was added dropwise to a stirring solution of 1 (4.0 g, 34.4 mmol) in dichloromethane (150 mL) at −40° C. under argon. Triethylamine (12.0 mL, 86.0 mmol) was then added dropwise, and the mixture was allowed to warm slowly to room temperature. After stirring for 16 hours, the mixture was quenched by addition of dilute hydrochloric acid (50 mL). The organic layer was separated, and the aqueous layer was further extracted with dichloromethane (2×50 mL). The combined organic fractions were washed with brine, dried (MgSO$_4$), and the solvent was evaporated under reduced pressure. The residue was chromatographed (SiO$_2$, heptane/ethyl acetate, 6:4) to give the mesylate 2 (6.1 g, 73%) as a white solid; R$_f$(heptane/ethyl acetate, 1:1) 0.18. $\delta^H$ (400 MHz; CDCl$_3$): 4.3 (4H, m), 3.05 (6H, s), 2.9 (2H, m), 2.2 (2H, m), 1.8 (2H m); $\delta_C$(400 MHz; CDCl$_3$): 69.51, 37.45, 35.28, 21.09.

Synthesis of Compound 3

Anhydrous lithium bromide (10.6 g, 121.8 mmol) was added to a stirring mixture of 2 (5.95 g, 24.4 mmol) in acetone (50 mL) under argon and the mixture was refluxed for 2 hours. After cooling, the acetone was evaporated under reduced pressure and the residue was taken up in ether (50 mL), washed with water (50 mL), brine, dried (MgSO$_4$), and the solvent was evaporated under reduced pressure. The residue was chromatographed (SiO$_2$, heptane/ethyl acetate, 95:5) to give the dibromide 3 (5.36 g, 86%) as an orange liquid; R$_f$(heptane-ethyl acetate, 8:2), 0.82. $\delta_H$ (400 MHz; CDCl$_3$): 3.6 (2H, m), 3.45 (2H, m), 2.85 (2H, m), 2.1 (2H, m), 1.7 (2H, m; $\delta_C$ (400 MHz; CDCl$_3$): 39.70, 33.79, 23.95.

Synthesis of Compound 4

To a cooled (0° C.) suspension of potassium hydride (1.58 g, 39.5 mmol) (previously washed 3 times with pentane) in tetrahydrofuran (22 mL) was added, under an argon atmosphere, a solution of methyl methylthiomethyl sulfoxide (1.36 mL, 13.04 mmol, previously dried over molecular sieves for 3 hours) in tetrahydrofuran (3 mL) over 1 hour. After stirring for a further 30 minutes, a solution of 3 (3.17 g, 13.1 mmol) in THF (2 mL) was added, at 0° C., over 1 hour. The reaction mixture was then allowed to warm up to room temperature and was stirred overnight. The mixture was quenched by addition of aqueous ammonium chloride (6 mL, 25%). After 10 minutes, the solid was filtered off and the filtrate concentrated. The residue was taken up in ether (20 mL) and 9N sulfuric acid (0.05 mL) was added. After stirring for 30 hours, saturated sodium hydrogen carbonate was added. The ether phase was separated and concentrated to 5 mL. Saturated sodium hydrogen sulphite (1.5 g) solution was added and the mixture stirred for 30 minutes. The phases were separated. The ethereal phase was stirred for further 30 minutes with a saturated sodium hydrogen sulphite (0.5 g) solution. The phases were separated and the collected aqueous phases were treated with aqueous sodium hydroxide (5 mL, 20%) and extracted with ether. The ether phase was dried (MgSO$_4$) and evaporated under reduced pressure to give 4 as a yellow liquid (0.16 g, 11%). $\delta_H$ (400 MHz; CDCl$_3$): 3.0 (2H, m), 2.15–2.45 (6H, m), 1.65 (2H, m).

Synthesis of Compound 5

Triethyl phosphonoacetate (0.32 mL, 1.61 mmol) was added dropwise to a stirring suspension of sodium hydride (0.059 g of a 60% dispersion in oil, 1.47 mmol) in THF (2 mL) at 0° C. under argon. After 20 minutes, ketone 4 (0.16 g, 1.45 mmol) in THF (1 mL) was added dropwise. The mixture was allowed to warm to room temperature and stirred for 16 hours. Water (5 mL) was added and the mixture was extracted with ethyl acetate. The combined organic fractions were washed with brine and dried (MgSO$_4$). The solvent was evaporated under reduced pressure. The residue was chromatographed (SiO$_2$, heptane/ethyl acetate, 95:5) to give the ester 5 (0.166 g, 0.92 mmol, 64%) as a colorless oil; $\delta_H$ (400 MHz; CDCl$_3$): 5.9 (1H, s), 4.2 (2H, q), 3.15 (1H, d), 2.9 (1H, m), 2.8 (1H, m); 2.65 (2H, m), 2.3 (1H, d), 2.15 (2H, m), 1.5 (2H, m), 1.3 (3H, t); $\delta_C$ (400 MHz; CDCl$_3$): 169.51, 166.98, 113.37, 59.62, 43.23, 38.79, 38.45, 36.20, 25.62, 24.95, 14.44.

Synthesis of Compound 6

Ester 5 (0.152 g, 0.84 mmol), nitromethane (0.092 mL, 1.7 mmol), and tetra-butylammonium fluoride (1.03 mL of a 1 M solution in THF, 1.03 mmol) were heated to 65° C. in THF (1 mL) for 4 hours. The mixture was allowed to cool, diluted with ether (30 mL), and acidified with 2N hydrochloric acid (5 mL). The organic layer was washed with brine, dried (MgSO$_4$), and the solvent was evaporated under reduced pressure. The residue was chromatographed (SiO$_2$, heptane/ether, 95:5) to give nitro-ester 6 (0.085 g, 0.35 mmol, 41%) as a colorless liquid; $\delta_H$ (400 MHz; CDCl$_3$): 4.4 (2H, s), 4.15 (2H, q), 2.75 (2H, bs), 2.7 (2H, s), 2.3 (2H, m); 2.1 (2H, m), 1.65 (4H, m), 1.15 (3H, t); $\delta_C$ (400 MHz; CDCl$_3$): 171.48, 79.68, 60.52, 50.10, 44.15, 41.06, 37.36, 25.76, 14.28.

Synthesis of Compounds 7A and 7B

Nitro-ester 6 (0.076 g, 0.31 mmol) in methanol (10 mL) was shaken over a catalytic amount of nickel sponge catalyst under a hydrogen atmosphere (50 Psi, 30° C.) for 12 hours. The mixture was filtered, and the solvent was evaporated under reduced pressure to give a mixture of lactam 7A and amino-ester 7B (0.05 g) as a white solid. This was used without further purification and characterization.

Synthesis of Compound 8

7A and 7B (0.05 g) were dissolved in hydrochloric acid (2 mL of a 6N solution), and the mixture was refluxed for 4 hours. After cooling, solvent was evaporated under reduced pressure to give the acid as a white solid. This was recrystallized using ethyl acetate/methanol to give pure 8 (0.045 g, 0.2 mmol, 64%); $\delta_H$ (400 MHz; D$_2$O): 3 (2H, s), 2.85 (4H, m+s), 2.35 (2H, m), 2.1 (2H, m), 1.75 (4H, m). $\delta_C$ (400 MHz; D$_2$O): 167.5, 46.64, 43.89, 42.03, 40.89, 36.08, 23.91. m/z (ES$^+$) 184 (M+H, 100%).

EXAMPLE 7

(±)-(1α, 5β)(3-aminomethyl-bicyclo[3.2.0]hepty-3-yl)-ascetic Acid Hydrochloride

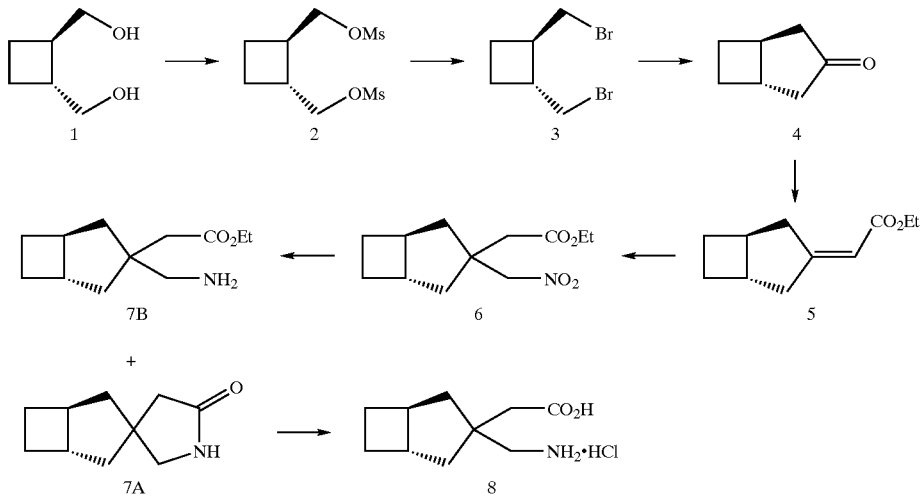

Synthesis of compound 1

Lithium aluminum hydride (134.8 mL of a 1 M solution in ether, 134.8 mmol) was added dropwise to a stirring solution of cis-cyclobutane-1,2-dicarboxylic acid (9.71 g, 67.39 mmol) in THF (120 mL) at 0° C. under argon. The mixture was allowed to warm to room temperature and stirred for 16 hours. The mixture was cooled to 0° C. and quenched by careful addition of water (5.2 mL), sodium hydroxide solution (5.2 mL of a 15% w/v solution), and water (15.7 mL). The mixture was stirred for 15 minutes, and the precipitate was removed by filtration. The solvent was evaporated under reduced pressure to give the alcohol 1 as a pale yellow oil (6.73 g, 57.64 mmol, 85%); $\delta_H$ (400 MHz; CDCl$_3$): 3.85 (2H, m), 3.6 (2H, m), 2.9 (2H, s), 2.7 (2H, m), 2 (2H, m); 1.55 (2H, m).

Synthesis of Compound 2

Mesyl chloride (29.3 mL, 373.8 mmol) was added dropwise to a stirring solution of 1 (8.85 g, 75.8 mmol) in dichloromethane (500 mL) at 40° C. under argon. Triethylamine (63.4 mL, 454.4 mmol) was then added dropwise, and the mixture was allowed to warm slowly to room temperature. After stirring for 16 hours, the mixture was quenched by addition of dilute hydrochloric acid (100 mL). The organic layer was separated, and the aqueous layer was further extracted with dichloromethane (2×100 mL). The combined organic fractions were washed with brine, dried (MgSO$_4$), and the solvent was evaporated under reduced pressure. The residue was chromatographed (SiO$_2$, heptane/ethyl acetate, 6:4) to give the mesylate 2 (15.89 g, 58.3 mmol, 77%) as a white solid; $\delta_H$ (400 MHz; CDCl$_3$): 3.0 (6H, m), 2.6 (2H, m), 2.05 (2H, m), 1.8 (2H, m).

Synthesis of Compound 3

Anhydrous lithium bromide (25 g, 287.3 mmol) was added to a stirring mixture of 2 (15.84 g, 57.4 mmol) in acetone (150 mL) under argon, and the mixture was refluxed for 2 hours. After cooling, the acetone was evaporated under reduced pressure, and the residue was taken up in ether (100 mL), washed with water (100 mL), brine, dried (MgSO$_4$), and the solvent was evaporated under reduced pressure to give the dibromide 3 (13.5 g, 55.8 mmol, 97%) as an orange liquid; $\delta_H$ (400 MHz; CDCl$_3$): 3.5 (4H, m), 2.45 (2H, m), 2.05 (2H, m), 1.6 (2H, m).

Synthesis of Compound 4

To a cooled (0° C.) suspension of potassium hydride (1.08 g, 27 mmol) (previously washed 3 times with pentane) in THF (15 mL) was added, under an argon atmosphere, a solution of methyl methylthiomethyl sulfoxide (0.93 mL, 8.92 mmol, previously dried over molecular sieves for 3 hours) in THF (2 mL) over a period of 1 hour. After siring for a further 30 minutes, a solution of 3 (2.16 g, 8.93 mmol) in THF (1 mL) was added, at 0° C., over a period of 1 hour. The reaction mixture was then allowed to warm up to room temperature and was stirred overnight. The mixture was quenched by addition of aqueous ammonium chloride (6 mL, 25%). After 10 minutes, the solid was filtered off and the filtrate concentrated. The residue was taken up in ether (20 mL), and 9N sulfuric acid (0.03 mL) was added. After stirring for 30 hours, saturated sodium hydrogen carbonate was added. The ether phase was separated and concentrated to 5 mL. Saturated sodium hydrogen sulphite (1.5 g) solution was added and the mixture stirred for 30 minutes. The phases were separated. The ethereal phase was stirred for further 30 minutes with a saturated sodium hydrogen sulphite (0.5 g) solution. The phases were separated and the collected aqueous phases were treated with aqueous sodium hydroxide (5 mL, 20%) and extracted with ether. The ether phase was dried (MgSO$_4$) and the solvent was evaporated under reduced pressure to give 4 as a yellow liquid (0.141 g, 15%); $\delta_H$ (400 MHz; CDCl$_3$): 2.25 (4H, m), 2.0 (4H, m), 1.7 (2H, m).

Synthesis of Compound 5

Triethyl phosphonoacetate (0.28 mL, 1.41 mmol) was added dropwise to a stirring suspension of sodium hydride (0.052 g of a 60% dispersion in oil, 1.29 mmol) in THF (2 mL) at 0° C. under argon. After 20 minutes, ketone 4 (0.141 g, 1.28 mmol) in THF (1 mL) was added dropwise. The mixture was allowed to warm to room temperature and stirred for 16 hours. Water (5 mL) was added, and the mixture was extracted. The combined organic fractions were washed with brine and dried (MgSO$_4$). The solvent was evaporated under reduced pressure. The residue was chromatographed (SiO$_2$, heptane\ethyl acetate, 95:5) to give the ester 5 (0.092 g, 0.51 mmol, 40%) as a colorless oil; $\delta_H$ (400 MHz; CDCl$_3$): 5.85 (1H, s), 4.1 (2H, q), 3.1 (1H, d.d), 2.45 (1H, d.d), 2.2 (2H, m), 1.75 (2H, m), 1.4 (2H, m), 1.25 (3H, t); $\delta_C$ (400 MHz; CDCl$_3$): 170.53, 166.57, 115.13, 59.62, 47.06, 45.69, 39.89, 37.24, 28.52, 28.17, 14.44.

Synthesis of Compound 6

Ester 5 (0.09 g, 0.5 mmol), nitromethane (0.055 mL, 1.02 mmol), and tetra-butylammonium fluoride (0.61 mL of a 1 M solution in THF, 0.61 mmol) were heated to 65° C. in THF (1 mL) for 4 hours. The mixture was allowed to cool, diluted with ether (30 mL), and acidified with 2N hydrochloric acid (5 mL). The organic layer was washed with brine, dried (MgSO$_4$), and the solvent was evaporated under reduced pressure. The residue was chromatographed (SiO$_2$, heptane/ether, 95:5) to give nitro-ester 6 (0.063 g, 0.26 mmol, 52%) as a colorless liquid. $\delta_H$ (400 MHz; CDCl$_3$): 4.65 (2H, [AB]q), 4.15 (2H, q), 2.65 (2H, [AB]q), 1.2–1.95 (3H, t and m, 13H); $\delta_C$ (400 MHz; CDCl$_3$): 171.28, 82.42, 60.56, 49.97, 45.80, 45.32, 42.88, 40.19, 40.09, 27.64, 14.26.

Synthesis of Compounds 7A and 7B

Nitro-ester 6 (0.063 g, 0.26 mmol) in methanol (10 mL) was shaken over a catalytic amount of nickel sponge catalyst under a hydrogen atmosphere (50 Psi, 30° C.) for 12 hours. The mixture was filtered, and the solvent was evaporated under reduced pressure to give a mixture of lactam 7A and amino-ester 7B (0.051 g) as a white solid. This was used without further purification and characterization.

Synthesis of Compound 8

7A and 7B (0.051 g) were dissolved in hydrochloric acid (2 mL of a 6N solution) and the mixture was refluxed for 4 hours. After cooling, solvent was evaporated under reduced pressure to give the acid as a white solid. This was recrystallized using ethyl acetate/methanol to give pure 8 (0.046 g, 0.21 mmol, 81%); $\delta_H$ (400 MHz; D$_2$O): 3.3 (2H, [AB]q), 2.7 (2H, [AB]q), 2 (2H, m), 1.35–1.85 (8H, m); $\delta_C$ (400 MHz; D$_2$O): 174.8, 47.50, 46.59, 44.28, 43.61, 41.64, 38.37, 38.09, 25.88. m/z (ES$^+$) 184 (M+H, 100%).

EXAMPLE 8

(1α,3β,5α)(3-Aminomethyl-bicyclo[3.2.0]hept-3-yl)-acetic Acid Hydrochloride

Synthesis of compound (2)

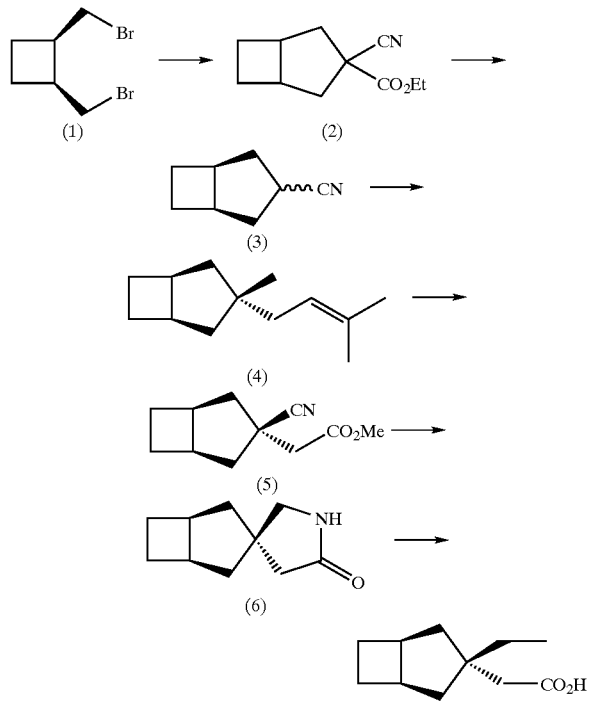

Dibromide 1 (5.7 g, 22.3 mmol), ethyl cyanoacetate (4.8 mL, 44.5 mmol) and potassium carbonate (6.15 g, 44.5 mmol) were stirred together in DMF (100 mL) for 48 hours. Dilute hydrochloric acid (100 mL) was added, and the mixture was extracted with ether (3×100 mL). The combined organic fractions were washed with brine, dried (MgSO$_4$), and the solvent was evaporated under reduced pressure. The residue was chromatographed (SiO$_2$, heptane-ethyl acetate, 98:2) to give the cyanoester 2 (4.3 g, 100%) as a 68:32 mixture of diastereoisomers; R$_f$(heptane-ethyl acetate, 9:1) 0.28; $v_{max}$(film)/cm$^{-1}$ 2241 (CN), 1741 (C=O); Major diastereoisomer: $\delta_H$(400 MHz; CDCl$_3$) 4.30 (2H, q, J7.1, CO$_2$CH$_2$Me), 2.98 (2H, m), 2.56–2.22 (6H, m), 1.70 (2H, m), 1.35 (3H, t, J7.1, Me); Minor diastereoisomer: $\delta_H$ (400 MHz; CDCl$_3$) 4.26 (2H, q, J7.1, CO$_2$CH$_2$Me), 3.05 (2H, m), 2.56–2.22 (6H, m), 1.99 (2H, m), 1.33 (3H, t, J7.1, Me).

Synthesis of Compound (3)

Cyanoester 2 (0.76 g, 3.91 mmol), water (0.14 mL, 7.82 mmol) and lithium chloride (0.66 g, 15.6 mmol) were heated to 150° C. in DMSO (40 mL) for 22 hours. The mixture was allowed to cool, diluted with water (150 mL) and extracted with ether (3×50 mL). The combined ether fractions were washed with brine, dried (MgSO$_4$), and the solvent was evaporated under reduced pressure. The residue was chromatographed (SiO$_2$, heptane-ethyl acetate, 95:5) to give the cyanide 3 (0.21 g, 44%) as a 60:40 mixture of diastereoisomers; R$_f$(heptane-ethyl acetate, 9:1) 0.44; $v_{max}$(film)/cm$^{-1}$ 2238 (CN); Major diastereoisomer: $\delta_H$ (400 MHz; CDCl$_3$) 2.97 (1H, m), 2.87 (2H, m), 2.32–2.18 (2H, m), 2.10–1.96 (3H, m), 1.92–1.78 (2H, m), 1.48–1.38 (1H, m); Minor diastereoisomer: $\delta_H$ (400 MHz; CDCl$_3$) 3.13 (1H, m), 2.87 (2H, m), 2.32–2.18 (2H, m), 2.10–1.96 (3H, m), 1.9–1.78 (2H, m), 1.48–1.38 (1H, m).

Synthesis of Compound (4)

Cyanide 3 (0.86 g, 7.1 mmol) in THF (30 mL) was added dropwise over 1 hour to a stirring mixture of lithium hexamethyldisilazide (7.8 mL of a 1 M solution in THF, 7.8 mmol) in THF (40 mL) at −78° C. under argon. The mixture was allowed to warm to −40° C. and stirred for 2 hours. The mixture was cooled to −78° C. and to dimethylallyl bromide (1.3 mL, 10.6 mmol) was added. The mixture was stirred for a further 2 hours at −78° C. and then allowed to warm to room temperature overnight. Saturated ammonium chloride solution (20 mL) was added, and the mixture was diluted with ether (50 mL) and dilute hydrochloric acid (30 mL). The aqueous layer was further extracted with ether (2×50 mL), and the combined organic fractions were washed with brine, dried (MgSO$_4$), and the solvent was evaporated under reduced pressure. The residue was chromatographed (SiO$_2$, heptane-ethyl acetate, 98:2) to give the cyanoalkene 4 (0.96 g, 72%) as a colorless oil; R$_f$(heptane-ethyl acetate, 95:5) 0.38; $v_{max}$(film)/cm$^{-1}$ 2230 (CN), 1673 (C=C); $\delta_H$ (400 MHz; CDCl$_3$) 5.27 (1H, tt, J7.6, 1.3, CHCMe2),2.89 (2H, m), 2.30–2.22 (4H, m), 2.10 (2H, d, J14.2), 1.94 (2H, m), 1.84–1.62 (2H, m), 1.65 (3H, s, Me), 1.55 (3H, s, Me); m/z (AP$^+$) 190 (M+H, 100%).

Synthesis of Compound (5)

Cyanoalkene 4 (0.96 g, 5.1 mmol) and sodium hydroxide (10.2 mL of a 2.5 M solution in methanol, 25.5 mmol) were stirred together in dichloromethane (80 mL) at −78° C. Ozone was passed through the mixture which immediately went orange. After 2 hours, the mixture turned to a green color, and the solution was purged with oxygen for 5 minutes and then with nitrogen. The stirring mixture was diluted with ether (100 mL) and water (100 mL) and allowed to warm to room temperature overnight. The aqueous layer was further extracted with ether (2×50 mL), and the combined organic fractions were washed with brine, dried (MgSO$_4$), and the solvent was evaporated under reduced pressure. The residue was chromatographed (SiO$_2$, heptane-ethyl acetate, 95:5) to give the cyanoester 5 (0.70 g, 71%) as a yellow oil; R$_f$(heptane-ethyl acetate, 8:2) 0.36; $v_{max}$(film)/cm$^1$ 2233 (CN), 1740 (C=O); 5H (400 MHz; CDCl$_3$) 3.75 (3H, s, OMe), 2.94 (2H, m), 2.63 (2H, s, CH$_2$CO$_2$Me), 2.35–2.21 (4H, m), 2.00 (2H, m), 1.86 (2H, m); m/z (AP$^+$) 194 (M+H, 95%).

Synthesis of Compound (6)

Cyanoester 5 (0.81 g, 4.2 mmol) in methanol (100 mL) was shaken over a catalytic amount of nickel sponge catalyst under a hydrogen atmosphere (60 Psi, 30° C.) for 6 hours. The mixture was filtered, and the solvent was evaporated under reduced pressure to give lactam 6 (0.64 g, 92%) as a white solid; $v_{max}$(film)/cm$^{-1}$ 1692 (C=O); $\delta_H$ (400 MHz; CDl$_3$ 5.52 (1H, br s, NH), 3.54 (2H, s, CH$_2$NH), 2.80 (2H, m), 2.26 (2H, m), 2.16 (2H, s, CH$_2$CO), 1.93 (2H, ddd, J 13.4, 8.1, 2.4), 1.74 (2H, dd, J13.0, 3.2), 1.64 (2H, m).

Synthesis of (1α,3β,5α)(3-Aminomethyl-bicyclo[3.2.0] hept-3-yl)-acetic Acid Hydrochloride Lactam 6 (0.64 g, 3.87 mmol) was dissolved in 1,4-dioxane (4 mL) and hydrochloric acid (16 mL of a 6N solution), and the mixture was refluxed for 6 hours. After cooling, the mixture was diluted with water (20 mL) and washed with dichloromethane (2×15 mL). The aqueous layer was evaporated under reduced pressure to give acid 7 (0.67 g, 79%) as a white solid. Recrystallization using ethyl acetate/methanol gave acid 7 exclusively (0.26 g); $\delta_H$ (400 MHz; d6-DMSO) 7.98 (2H, br s, NH$_2$), 3.13 (2H, s, CH$_2$NH$_2$), 2.70 (2H, s), 2.17–2.14 (4H, m), 1.85 (2H, dd, J13.3, 8.0), 1.63 (2H, m), 1.55 (2H, dd, J12.9, 5.1); m/z (ES$^+$) 184 (M+H, 100%); LCMS (Prodigy C18, 50 mm×4.6 mmid column, 5–50% Acetonitrile/water) Retention Time= 2.40 minutes, 98% purity.

The following compounds are made by one of the above methods:

(1α,5β)(3-Aminomethyl-bicyclo[3.1.0]hex-3-yl)-acetic acid, (1α,5β)(3-Aminomethyl-bicyclo[3.2.0]hept-3-yl)-acetic acid, (1α,5β)(2-Aminomethyl-octahydro-pentalen-2-yl)-acetic acid, (1α,6β)(2-Aminomethyl-octahydro-inden-2-yl)-acetic acid, (1α,7β)(2-Aminomethyl-decahydro-azulen-2-yl)-acetic acid, (1α,5β)(3-Aminomethyl-bicyclo[3.1.0]hex-3-yl)-acetic acid, (1α,5β)(3-Aminomethyl-bicyclo[3.2.0]hept-3-yl)-acetic acid, (1α,5β)(2-Aminomethyl-octahydro-pentalen-2-yl)-acetic acid, (1α,6β)(2-Aminomethyl-octahydro-inden-2-yl)-acetic acid, (1α,7β)(2-Aminomethyl-decahydro-azulen-2-yl)-acetic acid, (1α,3α,5α)(3-Aminomethyl-bicyclo[3.1.0]hex-3-yl)-acetic acid, (1α,3α,5α)(3-Aminomethyl-bicyclo[3.2.0]hept-3-yl)-acetic acid, (1α,3α,5α)(2-Aminomethyl-octahydro-pentalen-2-yl)-acetic acid, (1α,6α,8α)(2-Aminomethyl-octahydro-inden-2-yl)-acetic acid, (1α,7α,9α)(2-Aminomethyl-decahydro-azulen-2-yl)-acetic acid, (1α,3β,5α)(3-Aminomethyl-bicyclo[3.1.0]hex-3-yl)-acetic acid, (1α,3β,5α)(3-Aminomethyl-bicyclo[3.2.0]hept-3-yl)-acetic acid, (1α,3β,5α)(2-Aminomethyl-octahydro-pentalen-2-yl)-acetic acid, (1α,6α,8β)(2-Aminomethyl-octahydro-inden-2-yl)-acetic acid, (1α,7α,9β)(2-Aminomethyl-decahydro-azulen-2-yl)-acetic acid, ((1R,3R,6R)-3-Aminomethyl-bicyclo[4.1.0]hept-3-yl)-acetic acid, ((1R,3S,6R)-3-Aminomethyl-bicyclo[4.1.0]hept-3-yl)-acetic acid, ((1S,3S,6S)-3-Aminomethyl-bicyclo[4.1.0]hept-3-yl)-acetic acid, ((1S,3R,6S)-3-Aminomethyl-bicyclo[4.1.0]hept-3-yl)-acetic acid, ((1R,3R,6S)-3-Aminomethyl-bicyclo[4.2.0]oct-3-yl)-acetic acid, ((1R,3S,6S)-3-Aminomethyl-bicyclo[4.2.0]oct-3-yl)-acetic acid, ((1S,3S,6R)-3-Aminomethyl-bicyclo[4.2.0]oct-3-yl)-acetic acid, ((1S,3R,6R)-3-Aminomethyl-bicyclo[4.2.0]oct-3-yl)-acetic acid, ((3αR,5R,7αS)-5-Aminomethyl-octahydro-inden-5-yl)-acetic acid, ((3αR,5S,7αS)-5-Aminomethyl-octahydro-inden-5-yl)-acetic acid, ((3αS,5S,7αR)-5-Aminomethyl-octahydro-inden-5-yl)-acetic acid, ((3αS,5R,7αR)-5-Aminomethyl-octahydro-inden-5-yl)-acetic acid, ((2R,4αS,8αR)-2-Aminomethyl-decahydro-naphthalen-2-yl)-acetic acid, ((2S,4αS,8αR)-2-Aminomethyl-decahydro-naphthalen-2-yl)-acetic acid, ((2S,4αR,8αS)-2-Aminomethyl-decahydro-naphthalen-2-yl)-acetic acid, ((2R,4αR,8αS)-2-Aminomethyl-decahydro-naphthalen-2-yl)-acetic acid, ((2R,4αS,9αR)-2-Aminomethyl-decahydro-benzocyclohepten-2-yl)-acetic acid, ((2S,4αS,9αR)-2-Aminomethyl-decahydro-benzocyclohepten-2-yl)-acetic acid, ((2S,4αR,9αS)-2-Aminomethyl-decahydro-benzocyclohepten-2-yl)-acetic acid, ((2R,4αR,9αS)-2-Aminomethyl-decahydro-benzocyclohepten-2-yl)-acetic acid, ((1R,3S,6S)-3-Aminomethyl-bicyclo[4.1.0]hept-3-yl)-acetic acid, ((1R,3R,6S)-3-Aminomethyl-bicyclo[4.1.0]hept-3-yl)-acetic acid, ((1S,3S,6R)-3-Aminomethyl-bicyclo[4.1.0]hept-3-yl)-acetic acid, ((1S,3R,6R)-3-Aminomethyl-bicyclo[4.1.0]hept-3-yl)-acetic acid, ((1R,3R,6R)-3-Aminomethyl-bicyclo[4.2.0]oct-3-yl)-acetic acid, ((1R,3S,6R)-3-Aminomethyl-bicyclo[4.2.0]oct-3-yl)-acetic acid, ((1S,3S,6S)-3-Aminomethyl-bicyclo[4.2.0]oct-3-yl)-acetic acid, ((1S,3R,6S)-3-Aminomethyl-bicyclo[4.2.0]oct-3-yl)-acetic acid, ((3αR,5R,7αR)-5-Aminomethyl-octahydro-inden-5-yl)-acetic acid, ((3αR,5S,7αR)-5-Aminomethyl-octahydro-inden-5-yl)-acetic acid, ((3αS,5S,7αS)-5-Aminomethyl-octahydro-inden-5-yl)-acetic acid, ((3αS,5R,7αS)-5-Aminomethyl-octahydro-inden-5-yl)-acetic acid, ((2R,4αR,8αR)-2-Aminomethyl-decahydro-naphthalen-2-yl)-acetic acid, ((2S,4αS,8αR)-2-Aminomethyl-decahydro-naphthalen-2-yl)-acetic acid, ((2S,4αR,8αS)-2-Aminomethyl-decahydro-naphthalen-2-yl)-acetic acid, ((2R,4αS,8αS)-2-Aminomethyl-decahydro-naphthalen-2-yl)-acetic acid, ((2R,4αR,9αR)-2-Aminomethyl-decahydro-benzocyclohepten-2-yl)-acetic acid, ((2S,4αR,9αR)-2-Aminomethyl-decahydro-benzocyclohepten-2-yl)-acetic acid, ((2S,4αS,9αS)-2-Aminomethyl-decahydro-benzocyclohepten-2-yl)-acetic acid, and ((2R,4αS,9αS)-2-Aminomethyl-decahydro-benzocyclohepten-2-yl)-acetic acid.

The following methods relate specifically to the preparation of (1α,3α,5α)(3-Aminomethyl-bicyclo[3.2.0]hept-3-yl)-acetic acid.

Method 1

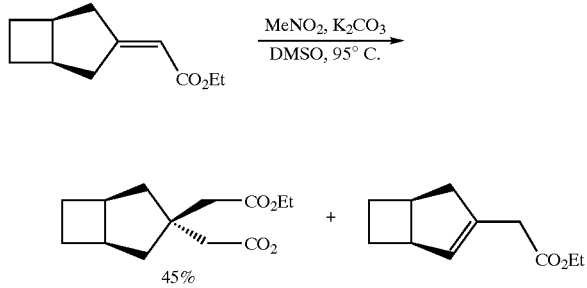

Nitromethane is added to the unsaturated ester in a solvent such as dimethylsulphoxide or N,N-dimethylformamide with a base such as potassium carbonate, sodium carbonate or cesium carbonate, at a temperature of from 0° C. to 120° C. This process achieves higher yields of the nitro ester and reduces the yield of de-conjugated ester compared to previous routes.

Method 2A

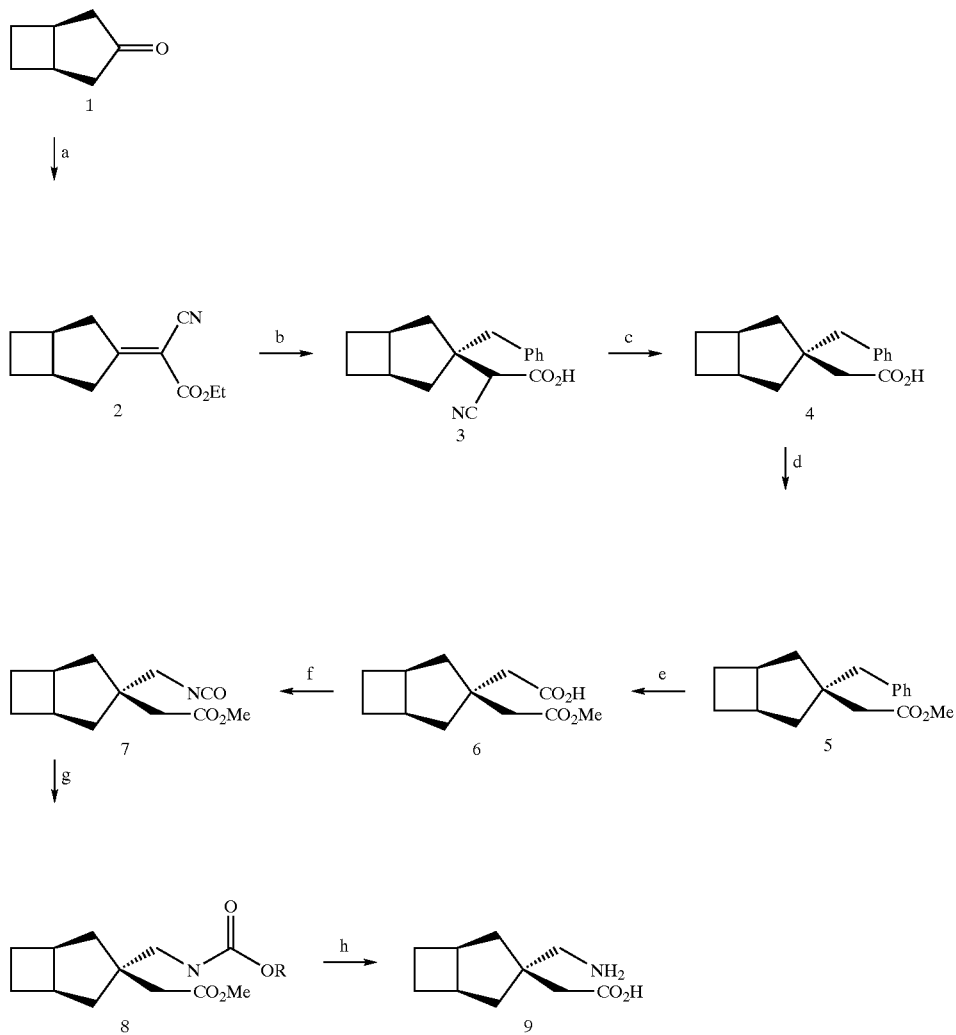

a) An alkyl cyanoacetate, for example ethyl cyanoacetate, is added to a mixture of cyclopentanone of formula (1) in a solvent selected from toluene, benzene, xylenes, or n-heptane to which acetic acid and β-alanine or ammonium acetate, or piperidine are added. The mixture is stirred at a temperature from 0° C. to 150° C. with removal of water by, for example, use of a Dean-Stark trap or activated molecular sieves, to produce the alkene of formula (2);

b) Adding the product of step a) above to a mixture of benzylmagnesium chloride or benzylmagnesium bromide or benzylmagnesium iodide, in a dry solvent selected from tetrahydrofuran, 1,4-dioxane, n-heptane, toluene, diethyl ether, or tert-butyl methyl ether at a temperature from −100° C. to 110° C. to produce the addition product of formula (3);

c) Adding the product of step b) above to a mixture of a base selected from potassium hydroxide, sodium hydroxide, lithium hydroxide, or cesium hydroxide in a solvent selected from ethylene glycol, 2-methoxyethyl ether, 1,4-dioxane, or diethylene glycol and stirring the mixture at a temperature from 25° C. to 250° C. to produce the carboxylic acid of formula (4);

d) Adding the product of step c) above to a mixture of iodomethane in a solvent selected from dichloromethane, chloroform, tetrahydrofuran, toluene, or 1,4-dioxane to which a base such as 1,8-diazabicyclo [5.4.0]undec-7-ene (DBU), triethylamine, or 1,5-diazabicyclo[4.3.0]non-5-ene (DBN) is added and stirred at a temperature from −40° C. to 110° C. to produce the ester of formula (5); or adding the product of step c) above to a mixture of methanol and a concentrated acid such as sulphuric acid or hydrochloric acid at a temperature ranging from 0° C. to 100° C.; or adding the product of step c) above to trimethylsilyldiazomethane and methanol in benzene or toluene at a temperature from 40° C. to 100° C.; or adding the product of step c) above to diazomethane in a solvent such as benzene, toluene, dichloromethane, or diethyl ether at a temperature from −40° C. to 40° C.;

e) Adding the product of step d) above to a mixture of carbon tetrachloride or ethyl acetate and acetonitrile towhich water, sodium periodate, and ruthenium (III) chloride are added, and stirred at a temperature from 40° C. to 80° C. to produce carboxylic acid of formula (6);

f) Adding the product of step e) above to a mixture of a base selected from triethylamine or diisopropylethylamine and a solvent selected from toluene, benzene, xylenes, tetrahydrofuran, diethyl ether, or n-heptane to which diphenylphosphoryl azide (DPPA) is added and stirring at a temperature from 0° C. to 150° C. to produce the isocyanate of formula (7); or adding the product of step e) above to ethyl chloroformate or isobutyl chloroformate and a base such as triethylamine or diisopropylethylamine in tetrahydrofuran or acetone or diethyl ether at a temperature of 40° C. to 78° C. followed by addition of sodium azide in water and tetrahydrofuran or acetone followed by addition of toluene or benzene and refluxing; and g) Adding the product of step f) above to a solvent selected from toluene, benzene, xylenes, or n-heptane to which methanol or tert-butanol was added to give (8) and then adding (8) to aqueous hydrochloric acid at a concentration of from 0.01 M to 12 M in the presence or absence of a solvent such as 1,4-dioxane, acetic acid or water to produce the amino acid (9); or adding the product of step f) above to a solvent selected from toluene, benzene, xylenes, or n-heptane to which benzyl alcohol was added to give (8) and then hydrogenating (8) over nickel or palladium or platinum to give lactam which was then hydrolysed using aqueous hydrochloric acid at a concentration of from 0.01 M to 12 M in the presence or absence of a solvent such as 1,4-dioxane, acetic acid, or water to produce the amino acid (9).

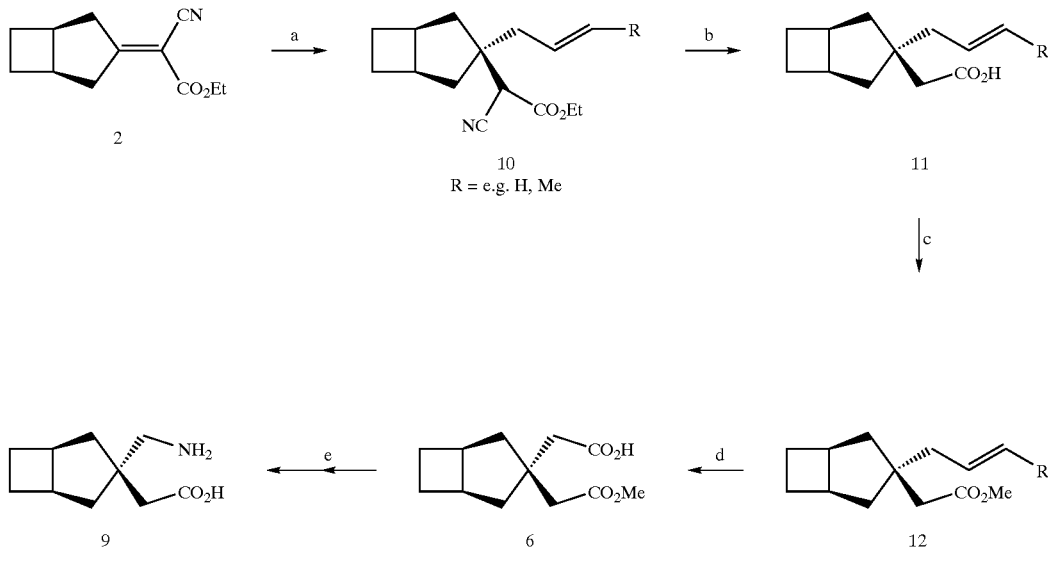

Method 2B a) Cyanoester (2) is added to allylmagnesium chloride or bromide or 2-butenylmagnesium chloride in a dry solvent selected from tetrahydrofuran, 1,4-dioxane, n-heptane, toluene, diethyl ether, or tert-butyl methyl ether at a temperature from −100° C. to 110° C. to produce the addition product of formula (10);

b) Adding the product of step a) above to a mixture of a base selected from potassium hydroxide, sodium hydroxide, lithium hydroxide, or cesium hydroxide in a solvent selected from ethylene glycol, 2-methoxyethyl ether, 1,4-dioxane, or diethylene glycol and stirring the mixture at a temperature from 25° C. to 250° C. to produce the carboxylic acid of formula (11);

c) Adding the product of step b) above to a mixture of iodomethane in a solvent selected from dichloromethane, chloroform, tetrahydrofuran, toluene, or 1,4-dioxane to which a base such as 1,8-diazabicyclo[5.4.0]undec-7-ene (DBU), triethylamine, or 1,5-diazabicyclo[4.3.0]non-5-ene (DBN) was added and stirred at a temperature from −40° C. to 110° C. to produce the ester of formula (11); or adding the product of step b) above to a mixture of methanol and a concentrated acid such as sulphuric acid or hydrochloric acid at a temperature ranging from 0° C. to 100° C.; or adding the product of step b) above to trimethylsilyldiazomethane and methanol in benzene or toluene at a temperature from 40° C. to 100° C.; or adding the product of step b) above to diazomethane in a solvent such as benzene, toluene, dichloromethane, or diethyl ether at a temperature from 40° C. to 40° C.; and d) Adding the product of step c) above to a mixture of carbon tetrachloride or ethyl acetate and acetonitrile to which water, sodium periodate, and ruthenium (III) chloride were added, and stirred at a temperature from 40° C. to 80° C. to produce carboxylic acid of formula (6).

Method 2C

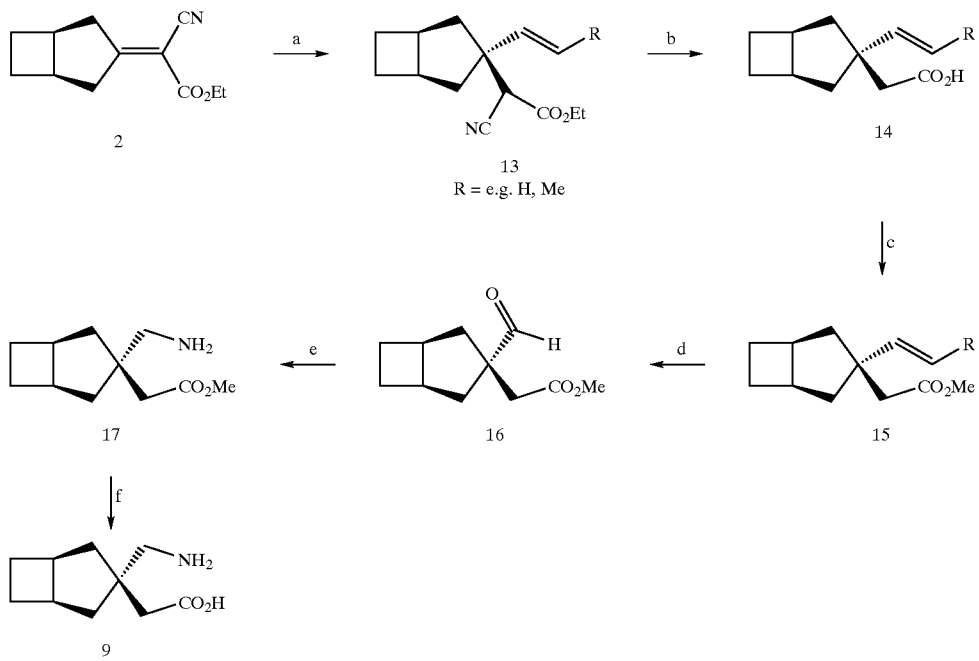

a) An organometallic reagent such as vinyllithium or vinylmagnesium chloride or bromide in a solvent such as tetrahydrofuran or diethyl ether at a temperature from −100° C. to 0° C. is added to the cyanoester (2) to give (13);

b) Adding the product of step a) above to a mixture of a base selected from potassium hydroxide, sodium hydroxide, lithium hydroxide, or cesium hydroxide in a solvent selected from ethylene glycol, 2-methoxyethyl ether, 1,4-dioxane, or diethylene glycol and stirring the mixture at a temperature from 25° C. to 250° C. to produce the carboxylic acid of formula (14);

c) Adding the product of step b) above to a mixture of iodomethane in a solvent selected from dichloromethane, chloroform, tetrahydrofuran, toluene, or 1,4-dioxane to which a base such as 1,8-diazabicyclo[5.4.0]undec-7-ene (DBU), triethylamine, or 1,5-diazabicyclo[4.3.0]non-5-ene (DBN) is added and stirred at a temperature from 40° C. to 110° C. to produce the ester of formula (15); or adding the product of step b) above to a mixture of methanol and a concentrated acid such as sulphuric acid or hydrochloric acid at a temperature ranging from 0° C. to 100° C.; or adding the product of step b) above to trimethylsilyldiazomethane and methanol in benzene or toluene at a temperature from −40° C. to 100° C.; or adding the product of step b) above to diazomethane in a solvent such as benzene, toluene, dichloromethane, or diethyl ether at a temperature from 40° C. to 40° C.;

d) The product of step c) above is ozonolysed in a solvent such as chloroform or dichloromethane or methanol followed by addition of a quench such as triphenylphosphine or dimethylsulphide at a temperature from −100° C. to 0° C. to give (16);

e) The product of step d) above in a solvent such as methanol or ethanol was reacted with ammonia solution or ammonia gas followed by reduction using sodium borohydride, sodium cyanoborohydride or sodium triacetoxyborohydride, or by reduction by hydrogenation in the presence of a catalyst such as nickel, palladium, or platinum to give (17); and f) The product of step e) above is hydrolysed using aqueous hydrochloric acid at a concentration of from 0.01 M to 12 M in the presence or absence of a solvent such as 1,4-dioxane, acetic acid, or water to produce the amino acid (9).

Method 3

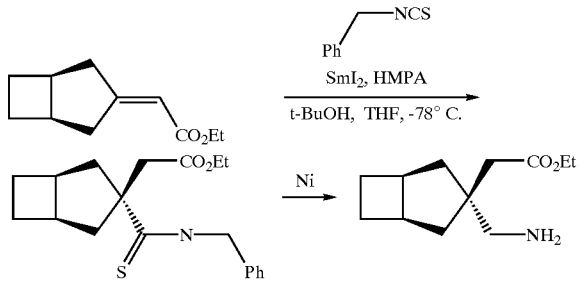

The unsaturated ester and benzyl thioisocyanate is stirred in a solvent mixture made up of tetrahydrofuran, diethyl ether, or 1,4-dioxane, a coordinating solvent such as HMPA or DMPU and an alcohol such as tert-butanol with samarium diiodide at a temperature of −100° C. to 0° C.; the resulting ester is hydrogenated in a solvent such as methanol, ethanol, ethyl acetate using a catalyst such as nickel, palladium, platinum, or rhodium at a temperature from 20° C. to 100° C. to give the amino acid.

Method 4A

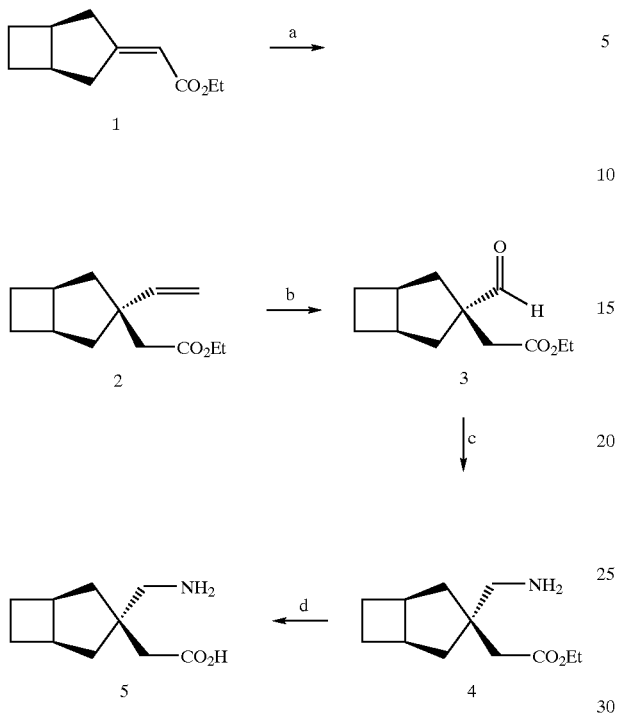

a) An organometallic reagent such as vinyllithium or vinylmagnesium chloride or bromide is mixed with dimethylzinc, zinc chloride, copper (I) iodide, copper (I) bromide dimethyl sulphide complex, or copper (I) cyanide in the presence of a Lewis acid such as boron trifluoride etherate or aluminium chloride in a solvent such as tetrahydrofuran or diethyl ether at a temperature from −100° C. to 0° C., and the unsaturated ester (1) is added to give addition product (2);

b) The product of step a) above is ozonolysed in a solvent such as chloroform or dichloromethane or methanol followed by addition of a quench such as triphenylphosphine or dimethylsulphide at a temperature from −100° C. to 0° C. to give (3);

c) The product of step b) above in a solvent such as methanol or ethanol was reacted with ammonia solution or ammonia gas followed by reduction using sodium borohydride, sodium cyanoborohydride or sodium triacetoxyborohydride, or by reduction by hydrogenation in the presence of a catalyst such as nickel, palladium, or platinum to give (4); and d) The product of step c) above is hydrolysed using aqueous hydrochloric acid at a concentration of from 0.01 M to 12 M in the presence or absence of a solvent such as 1,4-dioxane, acetic acid, or water to produce the amino acid (5).

Method 4B

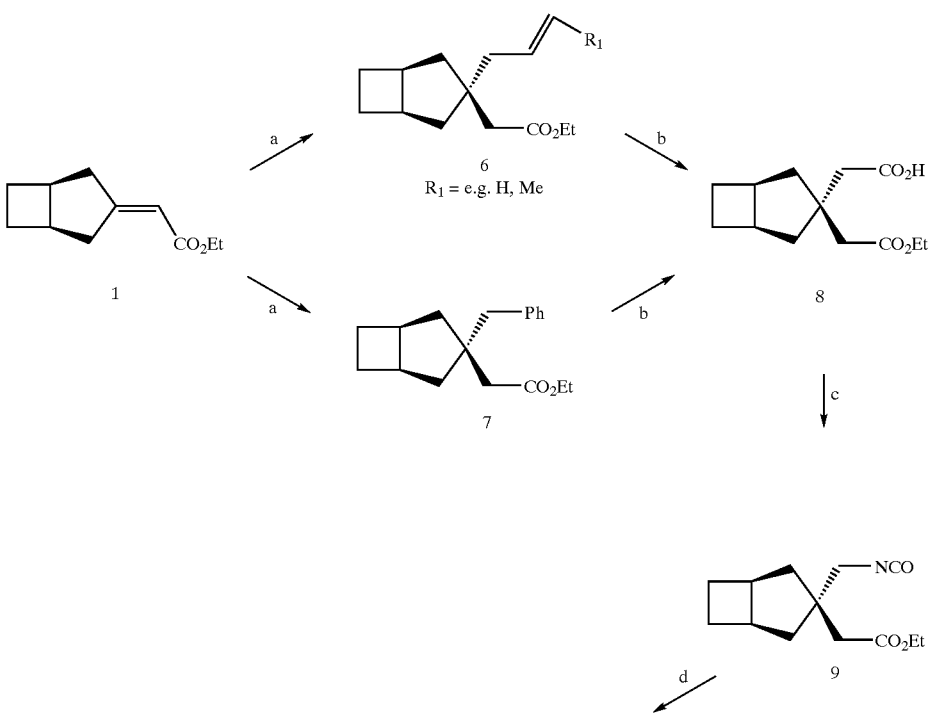

-continued

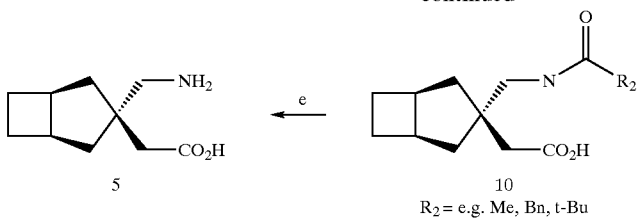

$R_2$ = e.g. Me, Bn, t-Bu a) An organometallic reagent such as allylmagnesium chloride or bromide is mixed with dimethylzinc, zinc chloride, copper (I) iodide, copper (I) bromide dimethyl sulphide complex, or copper (I) cyanide in the presence of a Lewis acid such as boron trifluoride etherate or aluminium chloride in a solvent such as tetrahydrofuran or diethyl ether at a temperature from −100° C. to 0° C. and the unsaturated ester (I) is added to give addition product (6); or an organometallic reagent such as benzylmagnesium chloride or bromide is mixed with dimethylzinc, zinc chloride, copper (I) iodide, copper (I) bromide dimethyl sulphide complex, or copper (I) cyanide in the presence of a Lewis acid such as boron trifluoride etherate or aluminium chloride in a solvent such as tetrahydrofuran or diethyl ether at a temperature from −100° C. to 0° C. and the unsaturated ester (1) is added to give addition product (7);

b) Adding the product of step a) above to a mixture of carbon tetrachloride or ethyl acetate and acetonitrile to which water, sodium periodate, and ruthenium (III) chloride are added, and stirred at a temperature from 40° C. to 80° C. to produce carboxylic acid of formula (8);

c) Adding the product of step b) above to a mixture of a base selected from triethylamine or diisopropylethylamine and a solvent selected from toluene, benzene, xylenes, tetrahydrofuran, diethyl ether, or n-heptane to which diphenylphosphoryl azide (DPPA) is added and stirring at a temperature from 0° C. to 150° C. to produce the isocyanate of formula (9); or adding the product of step b) above to ethyl chloroformate or isobutyl chloroformate and a base such as triethylamine or diisopropylethylamine in tetrahydrofuran or acetone or diethyl ether at a temperature of 40° C. to 78° C. followed by addition of sodium azide in water and tetrahydrofuran or acetone followed by addition of toluene or benzene and refluxing;

d) Adding the product of step c) above to a solvent selected from toluene, benzene, xylenes, or n-heptane to which methanol or tert-butanol was added to give (10) and then adding (10) to aqueous hydrochloric acid at a concentration of from 0.01 M to 12 M in the presence or absence of a solvent such as 1,4-dioxane, acetic acid, or water to produce the amino acid (5); or adding the product of step c) above to a solvent selected from toluene, benzene, xylenes, or n-heptane to which benzyl alcohol was added to give (10) and then hydrogenating (10) over nickel or palladium or platinum to give lactam which was then hydrolysed using aqueous hydrochloric acid at a concentration of from 0.01 M to 12 M in the presence or absence of a solvent such as 1,4-dioxane, acetic acid, or water to produce the amino acid (5).

Method 5

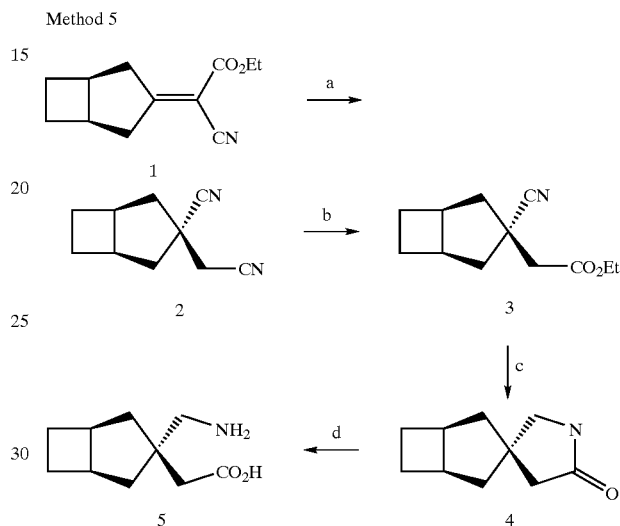

a) Compound (1) and potassium cyanide or sodium cyanide and water and ethanol or methanol are refluxed together with removal of water by, for example, use of a Dean-Stark trap to give (2);

b) the product of step a) is stirred with ethanol and toluene or benzene, and the solution is saturated with gaseous hydrochloric acid at a temperature from −30° C. to 40° C. to give (3);

c) the product of step b) above is hydrogenated in methanol, ethanol, or ethyl acetate using a catalyst such as nickel, palladium, platinum, or rhodium at a temperature from 15° C. to 60° C. to give (4);

d) the product of step c) above is hydrolysed using aqueous hydrochloric acid at a concentration of from 0.01 m to 12 m in the presence or absence of a solvent such as 1,4-dioxane, acetic acid, or water to produce the amino acid (5).

What is claimed is:

1. A compound of formula

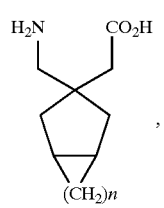

I

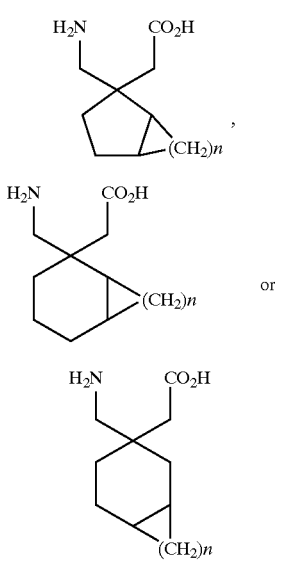

or a pharmaceutically acceptable salt thereof, or a prodrug thereof, wherein n is an integer of from 1 to 4.

2. A compound according to claim 1 wherein n is an integer of from 2 to 4.

3. A compound according to claim 1 wherein the compound is a compound of Formula I.

4. A compound according to claim 1 and selected from: add name for (1α,6α,8β)(2-Aminomethyl-octahydro-inden-2-yl)-acetic acid; (2-Aminomethyl-octahydro-inden-2-yl)-acetic acid; (2-Aminomethyl-octahydro-pentalen-2-yl)-acetic acid; (2-Aminomethyl-octahydro-pentalen-2-yl)-acetic acid; (3-Aminomethyl-bicyclo[3.2.0]hept-3-yl)-acetic acid; (3-Aminomethyl-bicyclo[3.2.0]hept-3-yl)-acetic acid; and (2-Aminomethyl-octahydro-inden-2-yl)-acetic acid.

5. A compound according to claim 1 and selected from:
(1α,5β)(3-Aminomethyl-bicyclo[3.1.0]hex-3-yl)-acetic acid,
(1α,5β)(3-Aminomethyl-bicyclo[3.2.0]hept-3-yl)-acetic acid,
(1α,5β)(2-Aminomethyl-octahydro-pentalen-2-yl)-acetic acid,
(1α,6β)(2-Aminomethyl-octahydro-inden-2-yl)-acetic acid,
(1α,7β)(2-Aminomethyl-decahydro-azulen-2-yl)-acetic acid,
(1α,5β)(3-Aminomethyl-bicyclo[3.1.0]hex-3-yl)-acetic acid,
(1α,5β)(3-Aminomethyl-bicyclo[3.2.0]hept-3-yl)-acetic acid,
(1α,5β)(2-Aminomethyl-octahydro-pentalen-2-yl)-acetic acid,
(1α,6β)(2-Aminomethyl-octahydro-inden-2-yl)-acetic acid,
(1α,7β)(2-Aminomethyl-decahydro-azulen-2-yl)-acetic acid,
(1α,3α,5α)(3-Aminomethyl-bicyclo[3.1.0]hex-3-yl)-acetic acid,
(1α,3α,5α)(2-Aminomethyl-octahydro-pentalen-2-yl)-acetic acid,
(1α,6α,8α)(2-Aminomethyl-octahydro-inden-2-yl)-acetic acid,
(1α,7α,9α)(2-Aminomethyl-decahydro-azulen-2-yl)-acetic acid,
(1α,3β,5α)(3-Aminomethyl-bicyclo[3.1.0]hex-3-yl)-acetic acid,
(1α,3β,5α)(3-Aminomethyl-bicyclo[3.2.0]hept-3-yl)-acetic acid,
(1α,3β,5α)(2-Aminomethyl-octahydro-pentalen-2-yl)-acetic acid,
(1α,6α,8β)(2-Aminomethyl-octahydro-inden-2-yl)-acetic acid,
(1α,7α,9β)(2-Aminomethyl-decahydro-azulen-2-yl)-acetic acid,
((1R,3R,6R)-3-Aminomethyl-bicyclo[4.1.0]hept-3-yl)-acetic acid,
((1R,3S,6R)-3-Aminomethyl-bicyclo[4.1.0]hept-3-yl)-acetic acid,
((1S,3S,6S)-3-Aminomethyl-bicyclo[4.1.0]hept-3-yl)-acetic acid,
((1S,3R,6S)-3-Aminomethyl-bicyclo[4.1.0]hept-3-yl)-acetic acid,
((1R,3R,6S)-3-Aminomethyl-bicyclo[4.2.0]oct-3-yl)-acetic acid,
((1R,3S,6S)-3-Aminomethyl-bicyclo[4.2.0]oct-3-yl)-acetic acid,
((1S,3S,6R)-3-Aminomethyl-bicyclo[4.2.0]oct-3-yl)-acetic acid,
((1S,3R,6R)-3-Aminomethyl-bicyclo[4.2.0]oct-3-yl) acetic acid,
((3αR,5R,7αS)-5-Aminomethyl-octahydro-inden-5-yl)-acetic acid,
((3αR,5S,7αS)-5-Aminomethyl-octahydro-inden-5-yl)-acetic acid,
((3αS,5S,7αR)-5-Aminomethyl-octahydro-inden-5-yl)-acetic acid,
((3αS,5R,7αR)-5-Aminomethyl-octahydro-inden-5-yl)-acetic acid,
((2R,4αS,8αR)-2-Aminomethyl-decahydro-naphthalen-2-yl)-acetic acid,
((2S,4αS,8αR)-2-Aminomethyl-decahydro-naphthalen-2-yl)-acetic acid,
((2S,4αR,8αS)-2-Aminomethyl-decahydro-naphthalen-2-yl)-acetic acid,
((2R,4αR,8αS)-2-Aminomethyl-decahydro-naphthalen-2-yl)-acetic acid,
((2R,4αS,9αR)-2-Aminomethyl-decahydro-benzocyclohepten-2-yl)-acetic acid,
((2S,4αS,9αR)-2-Aminomethyl-decahydro-benzocyclohepten-2-yl)-acetic acid,
((2S,4αR,9αS)-2-Aminomethyl-decahydro-benzocyclohepten-2-yl)-acetic acid,
((2R,4αR,9αS)-2-Aminomethyl-decahydro-benzocyclohepten-2-yl)-acetic acid,
((1R,3R,6S)-3-Aminomethyl-bicyclo[4.1.0]hept-3-yl)-acetic acid,
((1R,3S,6S)-3-Aminomethyl-bicyclo[4.1.0]hept-3-yl)-acetic acid,
((1S,3S,6R)-3-Aminomethyl-bicyclo[4.1.0]hept-3-yl)-acetic acid,
((1S,3R,6R)-3-Aminomethyl-bicyclo[4.1.0]hept-3-yl)-acetic acid,
((1R,3R,6R)-3-Aminomethyl-bicyclo[4.2.0]oct-3-yl)-acetic acid, ((1R,3S,6R)-3-Aminomethyl-bicyclo[4.2.0]oct-3-yl)-acetic acid, ((1S,3S,6S)-3-Aminomethyl-bicyclo[4.2.0]oct-3-yl)-acetic acid, ((1S,3R,6S)-3-Aminomethyl-bicyclo[4.2.0]oct-3-yl)-acetic acid, ((3αR,5R,7αR)-5-Aminomethyl-octahydro-inden-5-yl)-acetic acid, ((3αR,5S,7αR)-5-Aminomethyl-octahydro-inden-5-yl)-acetic acid, ((3αS,5S,7αS)-5-Aminomethyl-octahydro-inden-5-yl)-acetic acid, ((3αS,5R,7αS)-5-Aminomethyl-octahydro-inden-5-yl)-acetic acid, ((2R,4αR,8αR)-2-Aminomethyl-decahydro-naphthalen-2-yl)-acetic acid, ((2S,4αS,8αR)-2-Aminomethyl-decahydro-naphthalen-2-yl)-acetic acid, ((2S,4αR,8αS)-2-Aminomethyl-decahydro-naphthalen-2-yl)-acetic acid, ((2R,4αS,8αS)-2-Aminomethyl-decahydro-naphthalen-2-yl)-acetic acid, ((2R,4αR,9αR)-2-Aminomethyl-decahydro-benzocyclohepten-2-yl)-acetic acid, ((2S,4αR,9αR)-2-Aminomethyl-decahydro-benzocyclohepten-2-yl)-acetic acid, ((2S,4αS,9αS)-2-Aminomethyl-decahydro-benzocyclohepten-2-yl)-acetic acid, and ((2R,4αS,9αS)-2-Aminomethyl-decahydro-benzocyclohepten-2-yl)-acetic acid.

6. A compound according to claim 1 named (1α,3α,5α)(3-Aminomethyl-bicyclo[3.2.0]hept-3-yl)-acetic acid.

7. A pharmaceutical composition comprising a therapeutically effective amount of a compound according to claim 1 and a pharmaceutically acceptable carrier.

8. A method for treating epilepsy comprising administering a therapeutically effective amount of a compound according to claim 1 to a mammal in need of said treatment.

9. A method for treating faintness attacks, hypokinesia, and cranial disorders comprising administering a therapeutically effective amount of a compound according to claim 1 to a mammal in need of said treatment.

10. A method for treating neurodegenerative disorders comprising administering a therapeutically effective amount of a compound according to claim 1 to a mammal in need of said treatment.

11. A method for treating depression comprising administering a therapeutically effective amount of a compound according to claim 1 to a mammal in need of said treatment.

12. A method for treating anxiety comprising administering a therapeutically effective amount of a compound according to claim 1 to a mammal in need of said treatment.

13. A method for treating panic comprising administering a therapeutically effective amount of a compound according to claim 1 to a mammal in need of said treatment.

14. A method for treating pain comprising administering a therapeutically effective amount of a compound according to claim 1 to a mammal in need of said treatment.

15. A method for treating neuropathological disorders comprising administering a therapeutically effective amount of a compound according to claim 1 to a mammal in need of said treatment.

16. A method for treating premenstrual syndrome comprising administering a therapeutically effective amount of a compound according to claim 1 to a mammal in need of said treatment.

* * * * *